(12) United States Patent
Chen et al.

(10) Patent No.: US 11,112,411 B2
(45) Date of Patent: Sep. 7, 2021

(54) METHOD FOR SIMULTANEOUS QUANTIFICATION OF ALXN1210 AND ECULIZUMAB IN HUMAN SERUM OR URINE

(71) Applicant: Alexion Pharmaceuticals, Inc., Boston, MA (US)

(72) Inventors: Meng Chen, Guilford, CT (US); Ryan Pelto, Middletown, CT (US)

(73) Assignee: Alexion Pharmaceuticals, Inc., Boston, MA (US)

( * ) Notice: Subject to any disclaimer, the term of this patent is extended or adjusted under 35 U.S.C. 154(b) by 100 days.

(21) Appl. No.: 16/497,999

(22) PCT Filed: Mar. 28, 2018

(86) PCT No.: PCT/US2018/024769
§ 371 (c)(1),
(2) Date: Sep. 26, 2019

(87) PCT Pub. No.: WO2018/183449
PCT Pub. Date: Oct. 4, 2018

(65) Prior Publication Data
US 2020/0033364 A1 Jan. 30, 2020

Related U.S. Application Data

(60) Provisional application No. 62/480,048, filed on Mar. 31, 2017.

(51) Int. Cl.
*G01N 33/68* (2006.01)
*C07K 16/18* (2006.01)
*C07K 16/40* (2006.01)

(52) U.S. Cl.
CPC ......... *G01N 33/6854* (2013.01); *C07K 16/18* (2013.01); *C07K 16/40* (2013.01); *G01N 33/6848* (2013.01)

(58) Field of Classification Search
CPC ........... G01N 33/6854; G01N 33/6848; C07K 16/18; C07K 16/40
See application file for complete search history.

(56) References Cited

U.S. PATENT DOCUMENTS

| 9,079,949 | B1 | 7/2015 | Andrien, Jr. et al. |
| 2004/0096876 | A1* | 5/2004 | Locke ............... G01N 33/6842 435/6.15 |
| 2012/0087862 | A1* | 4/2012 | Hood ............... A61P 35/00 424/9.1 |
| 2018/0106815 | A1* | 4/2018 | Barnidge ........... A61K 39/3955 |

FOREIGN PATENT DOCUMENTS

WO 2016/018978 A1 2/2016

OTHER PUBLICATIONS

Ladwig (I) (J. Am. Soc. Mass Spectrom. 2017 28:811-817 ; online publication Sep. 2016). (Year: 2017).*
Beck et al. (Analytical Chemistry 2012 84: 4637-4646) (Year: 2016).*
Mant et al. "HPLC Analysis and Purification of Peptides" In Methods in Molecular Biology 2007 vol. 386, total 53 pages (Year: 2007).*
Wehling et al. (Clinical and Experimental Immunology (Feb. 2016), p. 304-315). (Year: 2016).*
International Preliminary Report on Patentability, PCT/US2018/024769, dated Oct. 1, 2019, 10 pages.
International Search Report and Written Opinion, PCT/US2018/024769, dated May 24, 2018, 15 pages.

* cited by examiner

*Primary Examiner* — Changhwa J Cheu
(74) *Attorney, Agent, or Firm* — Nelson Mullins Riley & Scarborough LLP; Jane E. Remillard, Esq.; Jill Gomy Sloper, Esq.

(57) ABSTRACT

Provided herein are methods for simultaneously detecting and quantifying antibodies which bind to the same target and have high sequence identity, such as eculizumab and ALXN1210, present together or alone in a biological sample.

28 Claims, 7 Drawing Sheets

Specification includes a Sequence Listing.

Sequences of eculizumab (EC) and ALXN1210

Light chain for both

DIQMTQSPSSLSASVGDRVTITCGASENIYGALNWYQQKPGKAPKLLIYGATNLADGVPSRFSGS
GSGTDFTLTISSLQPEDFATYYCQNVLNTPLTFGQGTKVEIKRTVAAPSVFIFPPSDEQLKSGTA
SVVCLLNNFYPREAKVQWKVDNALQSGNSQESVTEQDSKDSTYSLSSTLTLSKADYEKHKVYA
CEVTHQGLSSPVTKSFNRGEC

Heavy chain for EC

QVQLVQSGAEVKKPGASVKVSCKASGYIFSNYWIQWVRQAPGQGLEWMGEILPGSGSTEYTEN
FKDRVTMTRDTSTSTVYMELSSLRSEDTAVYYCARYFFGSSPNWYFDVWGQGTLVTVSSASTK
GPSVFPLAPCSRSTSESTAALGCLVKDYFPEPVTVSWNSGALTSGVHTFPAVLQSSGLYSLSSVVT
VPSSNFGTQTYTCNVDHKPSNTKVDKTVERKCCVECPPCPAPPVAGPSVFLFPPKPKDTLMISRTP
EVTCVVVDVSQEDPEVQFNWYVDGVEVHNAKTKPREEQFNSTYRVVSVLTVLHQDWLNGKEY
KCKVSNKGLPSSIEKTISKAKGQPREPQVYTLPPSQEEMTKNQVSLTCLVKGFYPSDIAVEWESN
GQPENNYKTTPPVLDSDGSFFLYSRLTVDKSRWQEGNVFSCSVMHEALHNHYTQKSLSLSLGK

Heavy chain for ALXN1210

QVQLVQSGAEVKKPGASVKVSCKASGHIFSNYWIQWVRQAPGQGLEWMGEILPGSGHTEYTEN
FKDRVTMTRDTSTSTVYMELSSLRSEDTAVYYCARYFFGSSPNWYFDVWGQGTLVTVSSASTK
GPSVFPLAPCSRSTSESTAALGCLVKDYFPEPVTVSWNSGALTSGVHTFPAVLQSSGLYSLSSVVT
VPSSNFGTQTYTCNVDHKPSNTKVDKTVERKCCVECPPCPAPPVAGPSVFLFPPKPKDTLMISRTP
EVTCVVVDVSQEDPEVQFNWYVDGVEVHNAKTKPREEQFNSTYRVVSVLTVLHQDWLNGKEY
KCKVSNKGLPSSIEKTISKAKGQPREPQVYTLPPSQEEMTKNQVSLTCLVKGFYPSDIAVEWESN
GQPENNYKTTPPVLDSDGSFFLYSRLTVDKSRWQEGNVFSCSVLHEALHSHYTQKSLSLSLGK

FIG.2

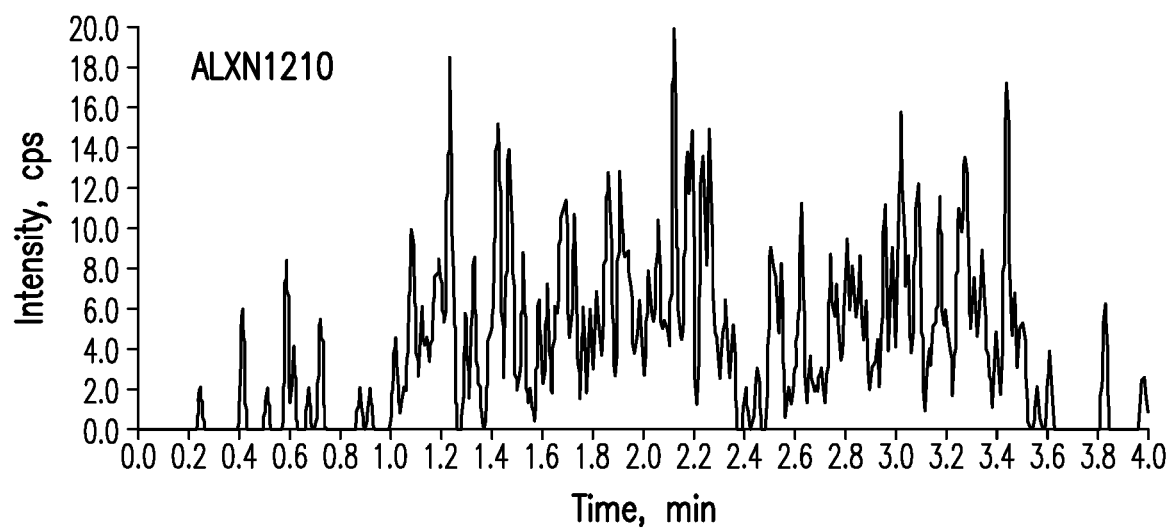
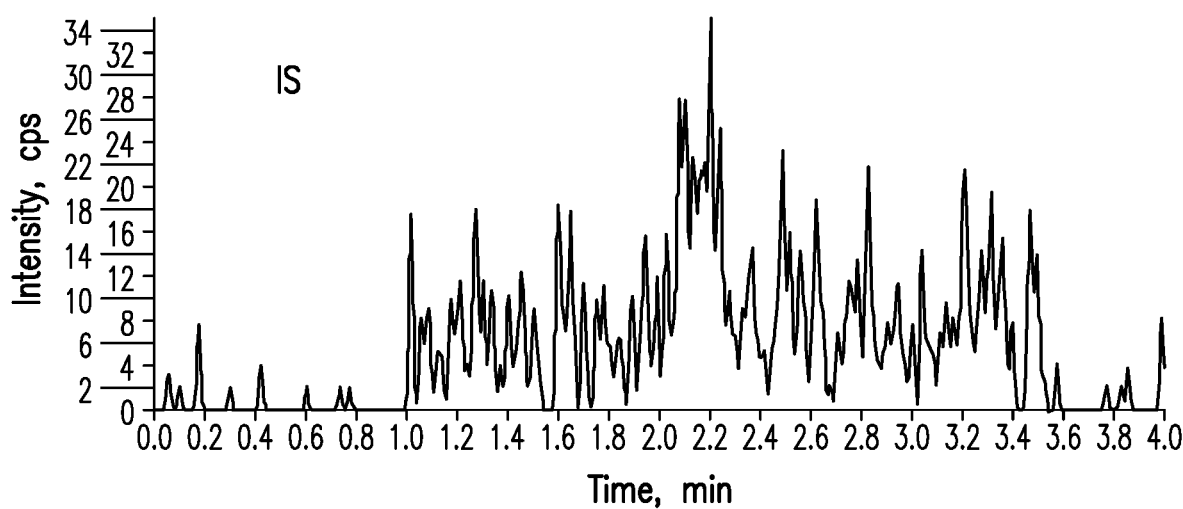
FIG.6

SEQUENCE LISTING

<160> NUMBER OF SEQ ID NOS: 22

<210> SEQ ID NO 1
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

```
<400> SEQUENCE: 1

Ala Ser Gly Tyr Ile Phe Ser Asn Tyr Trp Ile Gln Trp Val Arg
1               5                   10                  15

<210> SEQ ID NO 2
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 2

Ala Ser Gly His Ile Phe Ser Asn Tyr Trp Ile Gln Trp Val Arg
1               5                   10                  15

<210> SEQ ID NO 3
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 3

Gly Tyr Ile Phe Ser Asn Tyr Trp Ile Gln
1               5                   10

<210> SEQ ID NO 4
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 4

Glu Ile Leu Pro Gly Ser Gly Ser Thr Glu Tyr Thr Glu Asn Phe Lys
1               5                   10                  15

Asp

<210> SEQ ID NO 5
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 5

Tyr Phe Phe Gly Ser Ser Pro Asn Trp Tyr Phe Asp Val
1               5                   10

<210> SEQ ID NO 6
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 6
```

Gly Ala Ser Glu Asn Ile Tyr Gly Ala Leu Asn
1               5                   10

<210> SEQ ID NO 7
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 7

Gly Ala Thr Asn Leu Ala Asp
1               5

<210> SEQ ID NO 8
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 8

Gln Asn Val Leu Asn Thr Pro Leu Thr
1               5

<210> SEQ ID NO 9
<211> LENGTH: 122
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 9

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ile Phe Ser Asn Tyr
            20                  25                  30

Trp Ile Gln Trp Val Arg Gln Ala Pro Gly Gln Gly Leu Glu Trp Met
        35                  40                  45

Gly Glu Ile Leu Pro Gly Ser Gly Ser Thr Glu Tyr Thr Glu Asn Phe
    50                  55                  60

Lys Asp Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Tyr Phe Phe Gly Ser Ser Pro Asn Trp Tyr Phe Asp Val Trp
            100                 105                 110

Gly Gln Gly Thr Leu Val Thr Val Ser Ser
        115                 120

<210> SEQ ID NO 10
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 10

```
Asp Ile Gln Met Thr Gln Ser Pro Ser Leu Ser Ala Ser Val Gly
1               5                  10                  15

Asp Arg Val Thr Ile Thr Cys Gly Ala Ser Glu Asn Ile Tyr Gly Ala
            20                  25                  30

Leu Asn Trp Tyr Gln Gln Lys Pro Gly Lys Ala Pro Lys Leu Leu Ile
            35                  40                  45

Tyr Gly Ala Thr Asn Leu Ala Asp Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Asn Val Leu Asn Thr Pro Leu
                85                  90                  95

Thr Phe Gly Gln Gly Thr Lys Val Glu Ile Lys
            100                 105
```

<210> SEQ ID NO 11
<211> LENGTH: 326
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 11

```
Ala Ser Thr Lys Gly Pro Ser Val Phe Pro Leu Ala Pro Cys Ser Arg
1               5                  10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Cys Cys Val Glu Cys Pro Pro Cys Pro Ala Pro
            100                 105                 110

Pro Val Ala Gly Pro Ser Val Phe Leu Phe Pro Pro Lys Pro Lys Asp
            115                 120                 125

Thr Leu Met Ile Ser Arg Thr Pro Glu Val Thr Cys Val Val Val Asp
    130                 135                 140

Val Ser Gln Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Tyr Arg Val Val Ser Val Leu Thr Val Leu His Gln Asp Trp
            180                 185                 190

Leu Asn Gly Lys Glu Tyr Lys Cys Lys Val Ser Asn Lys Gly Leu Pro
            195                 200                 205

Ser Ser Ile Glu Lys Thr Ile Ser Lys Ala Lys Gly Gln Pro Arg Glu
    210                 215                 220

Pro Gln Val Tyr Thr Leu Pro Pro Ser Gln Glu Glu Met Thr Lys Asn
225                 230                 235                 240
```

Gln Val Ser Leu Thr Cys Leu Val Lys Gly Phe Tyr Pro Ser Asp Ile
            245                 250                 255

Ala Val Glu Trp Glu Ser Asn Gly Gln Pro Glu Asn Asn Tyr Lys Thr
            260                 265                 270

Thr Pro Pro Val Leu Asp Ser Asp Gly Ser Phe Phe Leu Tyr Ser Arg
            275                 280                 285

Leu Thr Val Asp Lys Ser Arg Trp Gln Glu Gly Asn Val Phe Ser Cys
            290                 295                 300

Ser Val Met His Glu Ala Leu His Asn His Tyr Thr Gln Lys Ser Leu
305                 310                 315                 320

Ser Leu Ser Leu Gly Lys
            325

<210> SEQ ID NO 12
<211> LENGTH: 448
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 12

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ile Phe Ser Asn Tyr
            20                  25                  30

Trp Ile Gln Trp Val Arg Gln Ala Pro Gly Gln Gly Leu Glu Trp Met
        35                  40                  45

Gly Glu Ile Leu Pro Gly Ser Gly Ser Thr Glu Tyr Thr Glu Asn Phe
    50                  55                  60

Lys Asp Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
            85                  90                  95

Ala Arg Tyr Phe Phe Gly Ser Ser Pro Asn Trp Tyr Phe Asp Val Trp
            100                 105                 110

Gly Gln Gly Thr Leu Val Thr Val Ser Ser Ala Ser Thr Lys Gly Pro
        115                 120                 125

Ser Val Phe Pro Leu Ala Pro Cys Ser Arg Ser Thr Ser Glu Ser Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
            165                 170                 175

Ala Val Leu Gln Ser Ser Gly Leu Tyr Ser Leu Ser Ser Val Val Thr
            180                 185                 190

Val Pro Ser Ser Asn Phe Gly Thr Gln Thr Tyr Thr Cys Asn Val Asp
        195                 200                 205

His Lys Pro Ser Asn Thr Lys Val Asp Lys Thr Val Glu Arg Lys Cys
    210                 215                 220

Cys Val Glu Cys Pro Pro Cys Pro Ala Pro Pro Val Ala Gly Pro Ser
225                 230                 235                 240

Val Phe Leu Phe Pro Pro Lys Pro Lys Asp Thr Leu Met Ile Ser Arg
            245                 250                 255

```
Thr Pro Glu Val Thr Cys Val Val Val Asp Val Ser Gln Glu Asp Pro
            260                 265                 270

Glu Val Gln Phe Asn Trp Tyr Val Asp Gly Val Glu Val His Asn Ala
        275                 280                 285

Lys Thr Lys Pro Arg Glu Glu Gln Phe Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Gly Leu Pro Ser Ser Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Gln Glu Glu Met Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Arg Leu Thr Val Asp Lys Ser
                405                 410                 415

Arg Trp Gln Glu Gly Asn Val Phe Ser Cys Ser Val Met His Glu Ala
            420                 425                 430

Leu His Asn His Tyr Thr Gln Lys Ser Leu Ser Leu Ser Leu Gly Lys
        435                 440                 445

<210> SEQ ID NO 13
<211> LENGTH: 214
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 13

Asp Ile Gln Met Thr Gln Ser Pro Ser Ser Leu Ser Ala Ser Val Gly
1               5                   10                  15

Asp Arg Val Thr Ile Thr Cys Gly Ala Ser Glu Asn Ile Tyr Gly Ala
            20                  25                  30

Leu Asn Trp Tyr Gln Gln Lys Pro Gly Lys Ala Pro Lys Leu Leu Ile
        35                  40                  45

Tyr Gly Ala Thr Asn Leu Ala Asp Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Asn Val Leu Asn Thr Pro Leu
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
```

165                 170                 175
Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 14
<211> LENGTH: 122
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 14

Gln Val Gln Leu Val Gln Ser Gly Ala Glu Val Lys Lys Pro Gly Ala
1               5                   10                  15

Ser Val Lys Val Ser Cys Lys Ala Ser Gly His Ile Phe Ser Asn Tyr
            20                  25                  30

Trp Ile Gln Trp Val Arg Gln Ala Pro Gly Gln Gly Leu Glu Trp Met
        35                  40                  45

Gly Glu Ile Leu Pro Gly Ser Gly His Thr Glu Tyr Thr Glu Asn Phe
    50                  55                  60

Lys Asp Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Tyr Phe Phe Gly Ser Ser Pro Asn Trp Tyr Phe Asp Val Trp
            100                 105                 110

Gly Gln Gly Thr Leu Val Thr Val Ser Ser
        115                 120

<210> SEQ ID NO 15
<211> LENGTH: 326
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 15

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Cys Cys Val Glu Cys Pro Pro Cys Pro Ala Pro
            100                 105                 110

```
Pro Val Ala Gly Pro Ser Val Phe Leu Phe Pro Pro Lys Pro Lys Asp
            115                 120                 125

Thr Leu Met Ile Ser Arg Thr Pro Glu Val Thr Cys Val Val Val Asp
130                 135                 140

Val Ser Gln Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Tyr Arg Val Val Ser Val Leu Thr Val Leu His Gln Asp Trp
            180                 185                 190

Leu Asn Gly Lys Glu Tyr Lys Cys Lys Val Ser Asn Lys Gly Leu Pro
            195                 200                 205

Ser Ser Ile Glu Lys Thr Ile Ser Lys Ala Lys Gly Gln Pro Arg Glu
            210                 215                 220

Pro Gln Val Tyr Thr Leu Pro Pro Ser Gln Glu Glu Met Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
            260                 265                 270

Thr Pro Pro Val Leu Asp Ser Asp Gly Ser Phe Phe Leu Tyr Ser Arg
            275                 280                 285

Leu Thr Val Asp Lys Ser Arg Trp Gln Glu Gly Asn Val Phe Ser Cys
            290                 295                 300

Ser Val Leu His Glu Ala Leu His Ser His Tyr Thr Gln Lys Ser Leu
305                 310                 315                 320

Ser Leu Ser Leu Gly Lys
                325

<210> SEQ ID NO 16
<211> LENGTH: 448
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 16

Gln Val Gln Leu Val Gln Ser Gly Ala Glu Val Lys Lys Pro Gly Ala
1               5                   10                  15

Ser Val Lys Val Ser Cys Lys Ala Ser Gly His Ile Phe Ser Asn Tyr
            20                  25                  30

Trp Ile Gln Trp Val Arg Gln Ala Pro Gly Gln Gly Leu Glu Trp Met
        35                  40                  45

Gly Glu Ile Leu Pro Gly Ser Gly His Thr Glu Tyr Thr Glu Asn Phe
    50                  55                  60

Lys Asp Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Tyr Phe Phe Gly Ser Ser Pro Asn Trp Tyr Phe Asp Val Trp
            100                 105                 110

Gly Gln Gly Thr Leu Val Thr Val Ser Ser Ala Ser Thr Lys Gly Pro
            115                 120                 125
```

Ser Val Phe Pro Leu Ala Pro Cys Ser Arg Ser Thr Ser Glu Ser Thr
130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
                180                 185                 190

Val Pro Ser Ser Asn Phe Gly Thr Gln Thr Tyr Thr Cys Asn Val Asp
            195                 200                 205

His Lys Pro Ser Asn Thr Lys Val Asp Lys Thr Val Glu Arg Lys Cys
210                 215                 220

Cys Val Glu Cys Pro Pro Cys Pro Ala Pro Pro Val Ala Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser Gln Glu Asp Pro
                260                 265                 270

Glu Val Gln Phe Asn Trp Tyr Val Asp Gly Val Glu Val His Asn Ala
            275                 280                 285

Lys Thr Lys Pro Arg Glu Glu Gln Phe Asn Ser Thr Tyr Arg Val Val
290                 295                 300

Ser Val Leu Thr Val Leu His Gln Asp Trp Leu Asn Gly Lys Glu Tyr
305                 310                 315                 320

Lys Cys Lys Val Ser Asn Lys Gly Leu Pro Ser Ser Ile Glu Lys Thr
                325                 330                 335

Ile Ser Lys Ala Lys Gly Gln Pro Arg Glu Pro Gln Val Tyr Thr Leu
                340                 345                 350

Pro Pro Ser Gln Glu Glu Met Thr Lys Asn Gln Val Ser Leu Thr Cys
            355                 360                 365

Leu Val Lys Gly Phe Tyr Pro Ser Asp Ile Ala Val Glu Trp Glu Ser
370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Arg Leu Thr Val Asp Lys Ser
                405                 410                 415

Arg Trp Gln Glu Gly Asn Val Phe Ser Cys Ser Val Leu His Glu Ala
                420                 425                 430

Leu His Ser His Tyr Thr Gln Lys Ser Leu Ser Leu Ser Leu Gly Lys
            435                 440                 445

<210> SEQ ID NO 17
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 17

Gly His Ile Phe Ser Asn Tyr Trp Ile Gln
1               5                   10

<210> SEQ ID NO 18
<211> LENGTH: 17
<212> TYPE: PRT

<210> SEQ ID NO 19
<211> LENGTH: 27
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 18

Glu Ile Leu Pro Gly Ser Gly His Thr Glu Tyr Thr Glu Asn Phe Lys
1               5                   10                  15

Asp

<210> SEQ ID NO 19
<211> LENGTH: 27
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 19

Gln Ala Pro Gly Gln Gly Leu Glu Trp Met Gly Glu Ile Leu Pro Gly
1               5                   10                  15

Ser Gly Ser Thr Glu Tyr Thr Glu Asn Phe Lys
            20                  25

<210> SEQ ID NO 20
<211> LENGTH: 23
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 20

Trp Gln Glu Gly Asn Val Phe Ser Cys Ser Val Met His Glu Ala Leu
1               5                   10                  15

His Asn His Tyr Thr Gln Lys
            20

<210> SEQ ID NO 21
<211> LENGTH: 27
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 21

Gln Ala Pro Gly Gln Gly Leu Glu Trp Met Gly Glu Ile Leu Pro Gly
1               5                   10                  15

Ser Gly His Thr Glu Tyr Thr Glu Asn Phe Lys
            20                  25

<210> SEQ ID NO 22
<211> LENGTH: 23
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 22

```
Trp Gln Glu Gly Asn Val Phe Ser Cys Ser Val Leu His Glu Ala Leu
1               5                   10                  15

His Ser His Tyr Thr Gln Lys
                20
```

METHOD FOR SIMULTANEOUS QUANTIFICATION OF ALXN1210 AND ECULIZUMAB IN HUMAN SERUM OR URINE

RELATED INFORMATION

This application is a 35 U.S.C. 371 national stage filing of International Application No. PCT/US2018/024769, filed on Mar. 28, 2018, which claims the benefit of the priority date of U.S. Provisional Application No. 62/480,048, filed on Mar. 31, 2017, the content of which is hereby incorporated by reference in its entirety.

SEQUENCE LISTING

The instant application contains a Sequence Listing which has been submitted electronically in ASCII format and is hereby incorporated by reference in its entirety. Said ASCII copy, created on Sep. 26, 2019, is named AXJ-231US_Sequence_Listing.txt and is 24,075 bytes in size.

BACKGROUND

The ability to accurately and reliably determine the pharmacokinetics of pharmaceutical compounds in a variety of preclinical models and clinical samples is essential to designing clinical trials and dosing regimens for determining optimal efficacy and minimal toxicity. This maximizes the chances for success in late-stage clinical trials and is a necessary component in the regulatory approval process. Due to their high likelihood for success and reduced development times and costs, therapeutic monoclonal antibodies (mAbs) are becoming increasingly important to the pharmaceutical industry. These proteins are based on naturally generated immunoglobulins (IgGs), but can be protein engineered to modify their natural properties and functions and to act by binding a target and inhibiting its activity or removing it from circulation. Monitoring mAb concentrations in serum is commonly performed by using enzyme-linked immunosorbent assays (ELISAs). This technique is sensitive and fast enough to efficiently analyze thousands of samples. However, it suffers from significant limitations when it comes to the quantification of antibodies which bind to the same target or different versions of the same antibody binding to the same target. In addition, immunoassays may be subject to matrix interferences and can have long development times. Furthermore, when moving between preclinical models, or from preclinical to clinical samples, or rehumanizing or otherwise re-engineering the antibody to reduce toxicological or immunological effects in the preclinical model and human clinical trials, the assay often needs to be redeveloped as drug development progresses. Thus, it would be useful to develop other methods to quantify mAbs that result in improved data quality and reduce development times and costs.

SUMMARY

Provided herein is a method for simultaneously detecting and quantifying antibodies which bind to the same target and have high sequence identity, such as eculizumab and ALXN1210 (ravulizumab), present together or alone in a biological sample (e.g., human serum or urine). This method is significant because while the two antibodies both bind the same target they differ only in four amino acids for the entire heavy and light chains.

In one aspect, the method comprises quantifying and detecting the respective amounts of eculizumab and ALXN1210 present together in a biological sample (e.g., human serum or urine) by: (a) treating the biological sample containing the antibodies with a protease to form a proteolytic peptide mixture of peptides from the antibodies in the biological sample, (b) analyzing a sample of the proteolytic peptide mixture by high performance liquid chromatography (HPLC) tandem mass spectrometry to detect a signature peptide from each of the antibodies in the biological sample, and (c) quantifying each antibody in the biological sample based on the signal ratio of its signature peptide to an internal control, wherein the internal control comprises a labeled form of the same signature peptide. In one embodiment, the signature peptide for eculizumab comprises or consists of SEQ ID NO: 1 and the signature peptide for ALXN1210 comprises or consists of SEQ ID NO: 2.

In another aspect, the method comprises detecting and quantifying the amount of eculizumab present in a biological sample (e.g., human serum or urine) by: (a) treating the biological sample containing the antibody with a protease to form a proteolytic peptide mixture of the antibody in the biological sample, (b) analyzing a sample of the proteolytic peptide mixture by high performance liquid chromatography (HPLC) tandem mass spectrometry to detect a signature peptide, and (c) quantifying the amount of eculizumab in the biological sample based on the signal ratio of the signature peptide to an internal control, wherein the internal control comprises a labeled form of the same signature peptide. In one embodiment, the signature peptide comprises or consists of SEQ ID NO: 1.

In another aspect, the method comprises detecting and quantifying the amount of ALXN1210 present in a biological sample (e.g., human serum or urine) by: (a) treating the biological sample containing the antibody with a protease to form a proteolytic peptide mixture of the antibody in the biological sample, (b) analyzing a sample of the proteolytic peptide mixture by high performance liquid chromatography (HPLC) tandem mass spectrometry to detect a signature peptide, and (c) quantifying the amount of ALXN1210 in the biological sample based on the signal ratio of the signature peptide to an internal control, wherein the internal control comprises a labeled form of the same signature peptide. In one embodiment, the signature peptide comprises or consists of SEQ ID NO: 2.

In a particular embodiment, a method of detecting and quantifying the respective amounts of two antibodies having high sequence identity present together in a biological sample (e.g., human serum or urine) is provided, wherein the antibodies are eculizumab and ALXN1210, the method comprising: (a) treating the biological sample containing the antibodies with a protease to form a proteolytic peptide mixture of the antibodies in the biological sample, (b) analyzing a sample of the proteolytic peptide mixture by high performance liquid chromatography (HPLC) tandem mass spectrometry to detect a signature peptide from each of the antibodies in the biological sample, wherein the signature peptide for eculizumab is selected from the group consisting of SEQ ID NO: 1, SEQ ID NO: 19, and SEQ ID NO: 20 and the signature peptide for ALXN1210 is selected from the group consisting of SEQ ID NO: 2, SEQ ID NO: 21, and SEQ ID NO: 22, and (c) quantifying each antibody in the biological sample based on the signal ratio of its signature peptide to an internal control, wherein the internal control comprises a labeled form of the same signature peptide.

In another embodiment, a method of detecting and quantifying the amount of an antibody present in a biological sample (e.g., human serum or urine) is provided, wherein the antibody is eculizumab, the method comprising: (a) treating the biological sample containing the antibody with a protease to form a proteolytic peptide mixture of the antibody in the biological sample, (b) analyzing a sample of the proteolytic peptide mixture by high performance liquid chromatography (HPLC) tandem mass spectrometry to detect a signature peptide, wherein the signature peptide for eculizumab is selected from the group consisting of SEQ ID NO: 1, SEQ ID NO: 19, and SEQ ID NO: 20, and (c) quantifying the amount of eculizumab in the biological sample based on the signal ratio of the signature peptide to an internal control, wherein the internal control comprises a labeled form of the same signature peptide.

In yet another embodiment, a method of detecting and quantifying the amount of an antibody present in a biological sample (e.g., human serum or urine) is provided, wherein the antibody is ALXN1210, the method comprising: (a) treating the biological sample containing the antibody with a protease to form a proteolytic peptide mixture of the antibody in the biological sample, (b) analyzing a sample of the proteolytic peptide mixture by high performance liquid chromatography (HPLC) tandem mass spectrometry to detect a signature peptide, wherein the signature peptide for ALXN1210 is selected from the group consisting of SEQ ID NO: 2, SEQ ID NO: 21, and SEQ ID NO: 22, and (c) quantifying the amount of ALXN1210 in the biological sample based on the signal ratio of the signature peptide to an internal control, wherein the internal control comprises a labeled form of the same signature peptide.

The methods described herein can included additional steps. For example, in one embodiment, the methods further comprise contacting the biological sample with an affinity capture reagent, such as bead-supported Protein A, prior to treating it with a protease (e.g., trypsin). In another embodiment, the method further comprises washing the Protein A bound antibodies to remove unbound components prior to proteolysis. In another embodiment, the method further comprises denaturing the antibody sample. In another embodiment, the method further comprises reducing the antibody sample. In another embodiment, the method further comprises alkylating the antibody sample. In one embodiment, the denaturation, reduction, and alkylation steps unfold the antibody protein and facilitates proteolytic digestion.

Any suitable mass spectrometry-based assay can be used in the methods described herein. In another embodiment, the mass spectrometry-based assay is reverse-phase UPLC-MS/MS.

The signature peptides for use in the methods described herein are no more than 20 amino acids in length. For example, in one embodiment, the signature peptide is no more than 20, 19, 18, 17, 16, or 15 amino acids in length. In one embodiment, the signature peptide comprises or consists of SEQ ID NO: 1. In another embodiment, the signature peptide comprises or consists of SEQ ID NO: 2. In one embodiment, the signature peptide for eculizumab is SEQ ID NO: 1. In another embodiment, the signature peptide for eculizumab is SEQ ID NO: 19. In another embodiment, the signature peptide for eculizumab is SEQ ID NO: 20. In another embodiment, the signature peptide for ALXN1210 is SEQ ID NO: 2. In another embodiment, the signature peptide for ALXN1210 is SEQ ID NO: 21. In yet another embodiment, the signature peptide for ALXN1210 is SEQ ID NO: 22.

Further provided are isolated peptides consisting of particular sequences. In one embodiment, an isolated peptide consisting of SEQ ID NO: 1 is provided. In another embodiment, an isolated peptide consisting of SEQ ID NO: 2 is provided. In yet another embodiment, an isolated peptide consisting of SEQ ID NO: 19 is provided. In a further embodiment, an isolated peptide consisting of SEQ ID NO: 20 is provided. In another embodiment, an isolated peptide consisting of SEQ ID NO: 21 is provided. In another embodiment an isolated peptide consisting of SEQ ID NO: 22 is provided.

BRIEF DESCRIPTION OF THE DRAWINGS

FIG. 2 shows the sequences of the heavy and light chains of eculizumab and ALXN1210. The four amino acid differences between eculizumab an ALXN1210 heavy chain sequences are underlined.

FIG. 6 shows a representative extracted ion chromatogram (XIC) of a blank sample.

DETAILED DESCRIPTION

Figure 1:
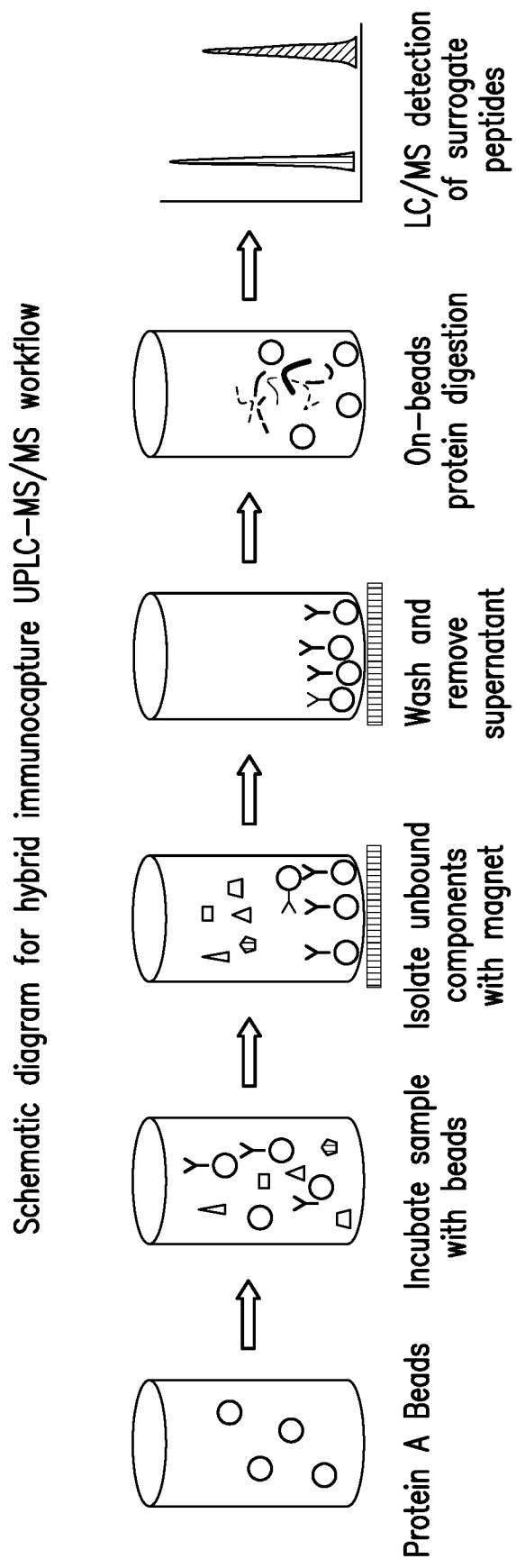
FIG. 1 is a schematic diagram of a hybrid immunocapture liquid chromatography mass spectrometry assay.

Eculizumab, also known as Soliris®, is a humanized monoclonal antibody manufactured in a single unit dosage form comprising 300 mg in 30 ml (10 mg/ml) solution for infusion and having binding specificity for the human complement protein C5. Eculizumab V regions and their humanization were described in U.S. Pat. No. 6,355,245, the teachings of which are hereby expressly incorporated by reference. Eculizumab is comprised of 1324 amino acids with a molecular mass of approximately 148 kDa.

The CDR1, CDR2 and CDR3 heavy chain sequences of eculizumab are shown in SEQ ID NOs: 3, 4, and 5, respectively. The CDR1, CDR2 and CDR3 light chain sequences of eculizumab are shown in SEQ ID NOs: 6, 7, and 8, respectively. The heavy chain variable region sequence of eculizumab is shown in SEQ ID NO: 9 and the light chain variable region sequence is shown in SEQ ID NO: 10. The heavy and light chain sequences of eculizumab are shown in SEQ ID NOs: 12 and 13, respectively.

ALXN1210 is an anti-C5 antibody described in PCT/US2015/019225 and U.S. Pat. No. 9,079,949, the teachings of which are hereby expressly incorporated by reference. ALXN1210 is a humanized monoclonal antibody that is highly structurally related to eculizumab. ALXN1210 was recently given the generic name ravulizumab and was derived through minimal targeted engineering of eculizumab by introducing four unique amino acid substitutions into the heavy chain, with the objective of enhancing the duration of terminal complement inhibition, while maintaining key eculizumab attributes such as epitope and low immunogenicity. Therefore, ravulizumab (ALXN1210) and eculizumab share over 99% primary sequence identity and have highly similar pharmacology, except ravulizumab has a T1/2 in humans of greater than 40 days as compared to eculizumab's T1/2 in human of approximately 12 days. Ravulizumab and ALXN1210 are used interchangeably herein. ALXN1210 selectively binds to human complement protein C5, inhibiting its cleavage to C5a and C5b during complement activation.

The CDR1, CDR2 and CDR3 heavy chain sequences of ALXN1210 are shown in SEQ ID NOs: 17, 18, and 5, respectively. The CDR1, CDR2 and CDR3 light chain sequences of ALXN1210 are shown in SEQ ID NOs: 6, 7, and 8, respectively. The heavy chain variable region sequence of ALXN1210 is shown in SEQ ID NO: 14. The light chain variable region sequence of ALXN1210 is shown in SEQ ID NO: 10. The entire heavy chain sequence of ALXN1210 is shown in SEQ ID NO: 16. The entire light chain sequence of ALXN1210 is shown in SEQ ID NO: 13.

The present disclosure addresses the important need for accurately quantifying eculizumab and ALXN1210 simultaneously in a biological sample from a patient (e.g., human serum or urine), particularly in a clinical setting where the patient is being switched from one antibody to the other during the course of treatment. The methods described herein can be adapted to switching from eculizumab to other anti-C-antibodies or other complement inhibitors. Such quantification is critical to determine accurate dosing regimens. Concurrent quantification of eculizumab and ALXN1210 has been extremely challenging due to the highly similar sequences of the two antibodies, which, as described, differ by only four amino acids, and because the antibodies bind to the same target. The methods described herein would be more easily adapted to switching from eculizumab to a an alternative complement inhibitor having more structural differences from eculizumab than does ALXN1210. Ligand binding assays, such as ELISA, quantify antibodies by their epitopes, and thus are insufficient to accurately quantify eculizumab and ALXN1210, because of the similarity in their sequence and the fact that these antibodies both bind to human C5 at the same epitope. Mass spectrometry relies on unique amino acid (peptide) sequences to distinguish among proteins. Accordingly, in view of the greater than 99% sequence identity between eculizumab and ALXN1210, prior mass spectrometry assays have lacked the necessary sensitivity or selectivity to discriminate between these antibodies. Moreover, this problem is exacerbated by the fact that human serum contains a multitude of endogenous antibodies, many of which also share regions of sequence identity and/or homology with eculizumab and ALXN1210, thus creating further noise and hindering accurate quantification of the antibodies.

The assay described in the present disclosure solves the above-discussed problem and provides experimental data demonstrating that the methods described herein can be used to reliably detect and quantify eculizumab and ALXN1210 in human serum and urine samples.

Digestion

In order to produce signature peptides for analysis by mass spectrometry, a biological sample such as serum or urine containing eculizumab and/or ALXN1210 is treated with a protease, either with or without an initial capture step, to form a digested antibody sample containing one or more signature peptides from the respective antibodies. The term "biological sample", as used herein, refers to any component derived or separated from an animal or human patient and includes urine, blood, plasma, and serum.

The term "signature peptide", as used herein, refers to a peptide that shows experimentally advantageous chromatographic and mass spectrometric properties and is unique (i.e., specific to eculizumab or ALXN1210). "Advantageous chromatographic performance", as used herein, can be defined as narrow peaks, low background noise with high peptide recovery. "Good mass spectrometric performance", as used herein, can be indicated by relatively high parent ion and fragment ion intensities with a high degree of selectivity for the sequence of the signature peptide. In one embodiment, the signature peptide is no more than 20, 19, 18, 17, 16, or 15 amino acids in length. In another embodiment, the signature peptide for eculizumab is selected from the group consisting of SEQ ID NO: 1, SEQ ID NO: 19, and SEQ ID NO: 20. In another embodiment, the signature peptide for ALXN1210 is selected from the group consisting of SEQ ID NO: 2, SEQ ID NO: 21, and SEQ ID NO: 22.

The term "protease", as used herein, refers to an enzyme capable of cleaving or hydrolyzing peptides or proteins into fragments in either a specific or generic, random manner. Example proteases include trypsin, papain, endoproteinase LysC, endoproteinase ArgC, staph aureus V8, chymotrypsin, Asp-N, Asn-C, pepsin, and endoproteinase GluC.

In one embodiment, prior to digestion, the biological sample is first contacted with an affinity capture reagent. After washing with an appropriate biological buffering system, an enriched biological sample is then eluted and treated with the protease. The term "affinity capture reagent", as used herein, refers to an antibody capture reagent or an antigen immobilized to a solid substrate. In one embodiment, the affinity capture reagent is Protein A or G. In another embodiment, the affinity capture reagent is the target antigen of the antibody or complement protein C5 or complement protein C5 attached to a solid substrate. In another embodiment, the affinity capture reagent is biotinylated. In another embodiment, the protein A or G is immobilized or conjugated onto a matrix and placed in a chromatography column format. In another embodiment, the protein A or G is immobilized on magnetic beads and the unbound material may be washed away and the bound antibodies may be digested by proteases while still attached to the beads.

After the biological sample is contacted and bound with the affinity reagent, it is then washed to remove non-specifically bound host proteins or other biomolecules. In a particular embodiment, the antibody bound to the affinity capture reagent is denatured to facilitate efficient elution from the affinity reagent and complete protease digestion. In one embodiment, the denaturation is performed using a surfactant. In one particular embodiment, the denaturation is performed using RAPIGEST™. In another particular embodiment, the denaturation is performed using PROTEASEMAX™. In certain embodiments, the antibody bound to the affinity reagent is also reduced to break any disulfide bonds and to further facilitate protease digestion. In a particular embodiment, reduction is performed using dithiothreitol (DTT). In another embodiment the reduced antibody is alkylated to prevent reformation of disulfide bonds. In one embodiment, alkylation is performed using iodoacetic acid.

High Performance Liquid Chromatography and Mass Spectrometry

Following digestion, the processed sample is analyzed using high performance liquid chromatography in tandem with mass spectrometry to quantitate the amount of each respective antibody present in the biological sample.

Mass spectrometry techniques are well known in the art (e.g., reviewed in Yates, et al., *Annu Rev Biomed Eng.* 2009; 11:49-79). In one embodiment, the mass spectrometry is performed by liquid chromatography/mass spectrometry (LC/MS). Other forms of mass spectrometry which can be employed include, for example, ultra performance liquid chromatography (UPLC) or tandem mass spectrometry (MS/MS). In a particular embodiment, reverse phase liquid chromatography tandem mass spectrometry (RPLC/MS/MS) is used. Ionization techniques which can be used include electron impact ionization (EI), chemical ionization (CI), desorption chemical ionization (DCI), fast atom bombardment (FAB), atmospheric pressure chemical ionization (APCI), electrospray ionization (ESI), matrix-assisted laser desorption/ionization (MALDI). Mass analyzers which can be employed include Quadrupole, Time-of-Flight (TOF), Orbitrap, and Linear ion trap. In some embodiments, the analyzers are used for tandem MS. In one embodiment, a triple quadruple mass analyzer is used.

As used herein, "chromatography" refers to a process in which a chemical mixture carried by a liquid or gas is separated into components as a result of differential distribution and separation of the chemical entities as they flow around or over a stationary liquid or solid phase.

As used herein, "liquid chromatography" (LC) means a process of separating the components of a fluid solution as the fluid uniformly flows through a column of a finely defined substance, particle or through capillary passageways. The separation results from the distribution of the components according to size and/or chemical characteristics of the mixture as differential amounts of time is spent associated between one or more stationary phases and the bulk fluid, (i.e., mobile phase), as this fluid moves relative to the stationary phase(s). Liquid chromatography includes high performance liquid chromatography (HPLC), reverse phase liquid chromatography (RPLC), and high turbulence liquid chromatography (HTLC), hydrophilic interaction liquid chromatography (HILIC), and normal phase liquid chromatography (NPLC).

The chromatographic column typically includes a medium (i.e., a packing material) to facilitate separation of chemical moieties (i.e., fractionation). The medium may include minute particles. The particles may include a bonded surface that covalently binds different chemical functional groups that interact with the various chemical moieties within the sample mixture to facilitate separation of the chemical moieties such as the signature peptides quantified in the experiments herein. Separation is often dependent on both size and chemical characteristic. One suitable bonded surface is a hydrophobic bonded surface such as an alkyl bonded surface. Alkyl bonded surfaces may include C4, C8, or C18 bonded alkyl groups to separate increasingly hydrophobic entities. The chromatographic column includes an inlet for receiving a sample and an outlet for discharging an effluent that includes the fractionated and separated sample components. The digested antibody sample is applied to the column at the inlet, eluted with a solvent or solvent mixture or solvent gradient, and discharged at the outlet. Different solvent modes may be selected for eluting different peptides of interest. For example, liquid chromatography may be performed using a gradient mode, an isocratic mode, or a polytyptic (i.e., mixed) mode. In one embodiment, the starting or sample loading solvent is an aqueous solvent with 5% organic modifier such as acetonitrile and elution occurs as the concentration of acetonitrile is increased to 50% over 50 minutes. In some embodiments, an additional mobile phase additive is used. In other embodiments, the mobile phase additive is DMSO.

The chromatographically separated components can be coupled with a mass spectrometer to measure the molecular weight of a particular fractionated species present in each peak eluting from the chromatography column. Data from mass spectrometry can then be used to detect and quantify the amount of signature peptide as it elutes from the column, and thus the respective amount of antibody present in the biological sample may be calculated and compared, using art recognized techniques as discussed below.

Quantification

Quantification of the signature peptides normalized to analogous internal standard peptides can be achieved using calculations from a standard curve.

In one embodiment, absolute quantifications of the signature peptides and the corresponding source antibodies are determined. Quantitative measurements of the signature peptides can be performed using internal standard peptides, such as the signature peptides in labeled form (i.e., so they are structurally and chemically similar to the signature peptides, but the mass is detectably different due to an isotopic label). Thus, the eluent from the separation process comprises an amount of the signature peptides that is in proportion to the known amount of the labeled internal standard peptides in the sample. It is then possible to relate the amount of the signature peptides in the sample to the amounts of the antibody from which it originated via the standard curve. In one embodiment, the internal standard peptides are isotopically labeled and incubated at a defined concentration with the antibody fragments. As used herein, "isotopically labeled" refers to a peptide that has been enriched synthetically with one or more heavy atom isotopes (e.g., stable isotopes such as Deuterium, $^{13}C$, $^{15}N$, $^{18}O$, $^{37}Cl$ or $^{81}Br$).

Methods

Provided herein are methods for simultaneously detecting and quantifying antibodies which bind to the same target and have high sequence identity, such as eculizumab and ALXN1210 (ravulizumab), present together or alone in a biological sample (e.g., human serum or urine).

In one aspect, the method comprises quantifying and detecting the respective amounts of eculizumab and ALXN1210 present together in a biological sample (e.g., human serum or urine) by: (a) treating the biological sample containing the antibodies with a protease to form a proteolytic peptide mixture of peptides from the antibodies in the biological sample, (b) analyzing a sample of the proteolytic peptide mixture by high performance liquid chromatography (HPLC) tandem mass spectrometry to detect a signature peptide from each of the antibodies in the biological sample, and (c) quantifying each antibody in the biological sample based on the signal ratio of its signature peptide to an internal control, wherein the internal control comprises a labeled form of the same signature peptide. In one embodiment, the signature peptide for eculizumab comprises or consists of SEQ ID NO: 1 and the signature peptide for ALXN1210 comprises or consists of SEQ ID NO: 2.

In another aspect, the method comprises detecting and quantifying the amount of eculizumab present in a biological sample (e.g., human serum or urine) by: (a) treating the biological sample containing the antibody with a protease to form a proteolytic peptide mixture of the antibody in the biological sample, (b) analyzing a sample of the proteolytic peptide mixture by high performance liquid chromatography (HPLC) tandem mass spectrometry to detect a signature peptide, and (c) quantifying the amount of eculizumab in the biological sample based on the signal ratio of the signature peptide to an internal control, wherein the internal control comprises a labeled form of the same signature peptide. In one embodiment, the signature peptide comprises or consists of SEQ ID NO: 1.

In another aspect, the method comprises detecting and quantifying the amount of ALXN1210 present in a biological sample (e.g., human serum or urine) by: (a) treating the biological sample containing the antibody with a protease to form a proteolytic peptide mixture of the antibody in the biological sample, (b) analyzing a sample of the proteolytic peptide mixture by high performance liquid chromatography (HPLC) tandem mass spectrometry to detect a signature peptide, and (c) quantifying the amount of ALXN1210 in the biological sample based on the signal ratio of the signature peptide to an internal control, wherein the internal control comprises a labeled form of the same signature peptide. In one embodiment, the signature peptide comprises or consists of SEQ ID NO: 2.

In one embodiment, a method of detecting and quantifying the respective amounts of two antibodies having high sequence identity present together in a biological sample (e.g., human serum or urine) is provided, wherein the antibodies are eculizumab and ALXN1210, the method comprising: (a) treating the biological sample containing the antibodies with a protease to form a proteolytic peptide mixture of the antibodies in the biological sample, (b) analyzing a sample of the proteolytic peptide mixture by high performance liquid chromatography (HPLC) tandem mass spectrometry to detect a signature peptide from each of the antibodies in the biological sample, wherein the signature peptide for eculizumab is selected from the group consisting of SEQ ID NO: 1, SEQ ID NO: 19, and SEQ ID NO: 20 and the signature peptide for ALXN1210 is selected from the group consisting of SEQ ID NO: 2, SEQ ID NO: 21, and SEQ ID NO: 22, and (c) quantifying each antibody in the biological sample based on the signal ratio of its signature peptide to an internal control, wherein the internal control comprises a labeled form of the same signature peptide.

In another embodiment, a method of detecting and quantifying the amount of an antibody present in a biological sample (e.g., human serum or urine) is provided, wherein the antibody is eculizumab, the method comprising: (a) treating the biological sample containing the antibody with a protease to form a proteolytic peptide mixture of the antibody in the biological sample, (b) analyzing a sample of the proteolytic peptide mixture by high performance liquid chromatography (HPLC) tandem mass spectrometry to detect a signature peptide, wherein the signature peptide for eculizumab is selected from the group consisting of SEQ ID NO: 1, SEQ ID NO: 19, and SEQ ID NO: 20, and (c) quantifying the amount of eculizumab in the biological sample based on the signal ratio of the signature peptide to an internal control, wherein the internal control comprises a labeled form of the same signature peptide.

In yet another embodiment, a method of detecting and quantifying the amount of an antibody present in a biological sample (e.g., human serum or urine) is provided, wherein the antibody is ALXN1210, the method comprising: (a) treating the biological sample containing the antibody with a protease to form a proteolytic peptide mixture of the antibody in the biological sample, (b) analyzing a sample of the proteolytic peptide mixture by high performance liquid chromatography (HPLC) tandem mass spectrometry to detect a signature peptide, wherein the signature peptide for ALXN1210 is selected from the group consisting of SEQ ID NO: 2, SEQ ID NO: 21, and SEQ ID NO: 22, and (c) quantifying the amount of ALXN1210 in the biological sample based on the signal ratio of the signature peptide to an internal control, wherein the internal control comprises a labeled form of the same signature peptide.

The methods described herein can included additional steps. For example, in one embodiment, the methods further comprise contacting the biological sample with an affinity capture reagent, such as bead-supported Protein A, prior to treating it with a protease (e.g., trypsin). In another embodiment, the method further comprises washing the Protein A bound antibodies to remove unbound components prior to proteolysis. In another embodiment, the method further comprises denaturing the antibody sample. In another embodiment, the method further comprises reducing the antibody sample. In another embodiment, the method further comprises alkylating the antibody sample. In one embodiment, the denaturation, reduction, and alkylation steps unfold the antibody protein and facilitates proteolytic digestion.

Isolated Peptides

Further provided are isolated peptides consisting of particular sequences. In one embodiment, an isolated peptide consisting of SEQ ID NO: 1 is provided. In another embodiment, an isolated peptide consisting of SEQ ID NO: 2 is provided. In yet another embodiment, an isolated peptide consisting of SEQ ID NO: 19 is provided. In a further embodiment, an isolated peptide consisting of SEQ ID NO: 20 is provided. In another embodiment, an isolated peptide consisting of SEQ ID NO: 21 is provided. In another embodiment an isolated peptide consisting of SEQ ID NO: 22 is provided.

Those skilled in the art will recognize, or be able to ascertain using no more than routine experimentation, many equivalents of the specific embodiments described herein. Such equivalents are intended to be encompassed by the following claims. In addition, all references cited throughout this application, are hereby incorporated by reference herein in their entireties, as though individually incorporated by reference. All sequence listing information also is part of the present disclosure.

EXAMPLES

Example 1: Hybrid Immunocapture UPLC-MS/MS Approach for Concurrent Detection and Quantification of ALXN1210 and Eculizumab in Human Serum To concurrently detect and quantify ALXN1210 and eculizumab in a human serum sample, the following hybrid immunocapture UPLC-MS/MS approach was developed (shown schematically in FIG. 1). Due to the high molecular weight of ALXN1210 and eculizumab, practical direct quantitative analysis using LC/triple quadruple mass spectrometric technology was not feasible. An immunoaffinity capture approach was developed to enrich ALXN1210 and eculizumab from human serum using magnetic beads coated with Protein A. The extracted natural antibodies and drug antibody proteins were subjected to on-bead proteolysis: denaturation with low concentration of organic solvents, reduction with dithiothreitol (DTT) at 60° C., alkylation with iodoacetic acid, and simultaneous or subsequent digestion with the protease trypsin. Next, characteristic "signature" peptides generated from each antibody after tryptic proteolysis were then used as surrogates for the detection and quantification of ALXN1210 and eculizumab in human serum using UPLC-MS/MS. Two signature tryptic peptides were selected for monitoring in the assay, as described below.

Example 2: Identification of Signature Peptide Sequences for ALXN1210 and Eculizumab ALXN1210 and eculizumab share significant sequence identity (i.e., only four amino acid differences exist between the two antibody drugs, as shown in FIG. 2). Accordingly, for specific detection of each antibody, signature peptides unique to each of ALXN1210 and eculizumab were generated using in silico tryptic digestion. Six peptides were selected which contained amino acid differences between the sequences of the two antibodies, as shown in Table 1.

TABLE 1

Eculizumab and ALXN1210 Signature Peptides

| SEQ ID NO | Amino Acid | Purpose |
|---|---|---|
| SEQ ID NO: 21 | QAPGQGLEWMGEIL PGSG<u>H</u>TEYTENFK | Quantification of ALXN1210 |
| SEQ ID NO: 22 | WQEGNVFSCSV<u>L</u>HE ALH<u>S</u>HYTQK | Quantification of ALXN1210 |
| SEQ ID NO: 2 | ASG<u>H</u>IFSNYWIQWVR | Quantification of ALXN1210 |
| SEQ ID NO: 19 | QAPGQGLEWMGEIL PGSG<u>S</u>TEYTENFK | Quantification of eculizumab |
| SEQ ID NO: 20 | WQEGNVFSCSV<u>M</u>HE ALH<u>N</u>HYTQK | Quantification of eculizumab |
| SEQ ID NO: 1 | ASG<u>Y</u>IFSNYWIQWVR | Quantification of eculizumab |

Example 3: Immunocapture of ALXN1210 and Eculizumab in Human Serum

An immunocapture assay was developed for the enrichment of ALXN1210 and eculizumab from human serum samples, as described below. Sensitivity was one of the major challenges for the development of the assay. The existence of endogenous proteins of high abundance from the other captured antibodies and other components in biological matrices leads to high background, significant ion suppression, and interferences of quantification. An immunocapture approach was examined using Protein A. Whole serum direct digestion was used as the control.

Protein A is a protein of microbial origin with the ability to bind to human IgG1, IgG2, and IgG4 with high affinity to the antibody Fc region. Even through both eculizumab and ALXN1210 contain a non-naturally occurring protein engineered heavy chain constructed with elements of both IgG2 and IgG4, both retain the ability to bind protein A. Protein A magnetic beads were incubated with human serum samples, during the period of incubation, IgGs from the sample were bound to the beads via their Fc regions (PURE-PROTEOME™ Protein A Magnetic Bead, EMD Millipore, Product No. LSKMAGA10). With the assistance of an external magnet (PUREPROTEOME™ Magnetic Stand, Millipore, Product No. LSKMAGS15), the IgG-Protein A bead complexes were separated and washed from other unbound serum components. Protease digestion was performed directly on bead-bound proteins using MS Grade Trypsin Protease, (Pierce Product No. 90305B).

For whole serum digestion, direct tryptic digestion of the sample was performed without any pre-treatment for the enrichment of target proteins or to reduce background. It was found that signature peptides were recovered using the whole serum digestion approach. The background was higher than was observed using other immunocapture approaches. However, the analyte responses (detection) from Protein A capture was high, resulting in excellent sensitivity and quantification. This technique using Protein A capture also showed high accuracy and precision when spiked QCs were examined.

Figure 3:
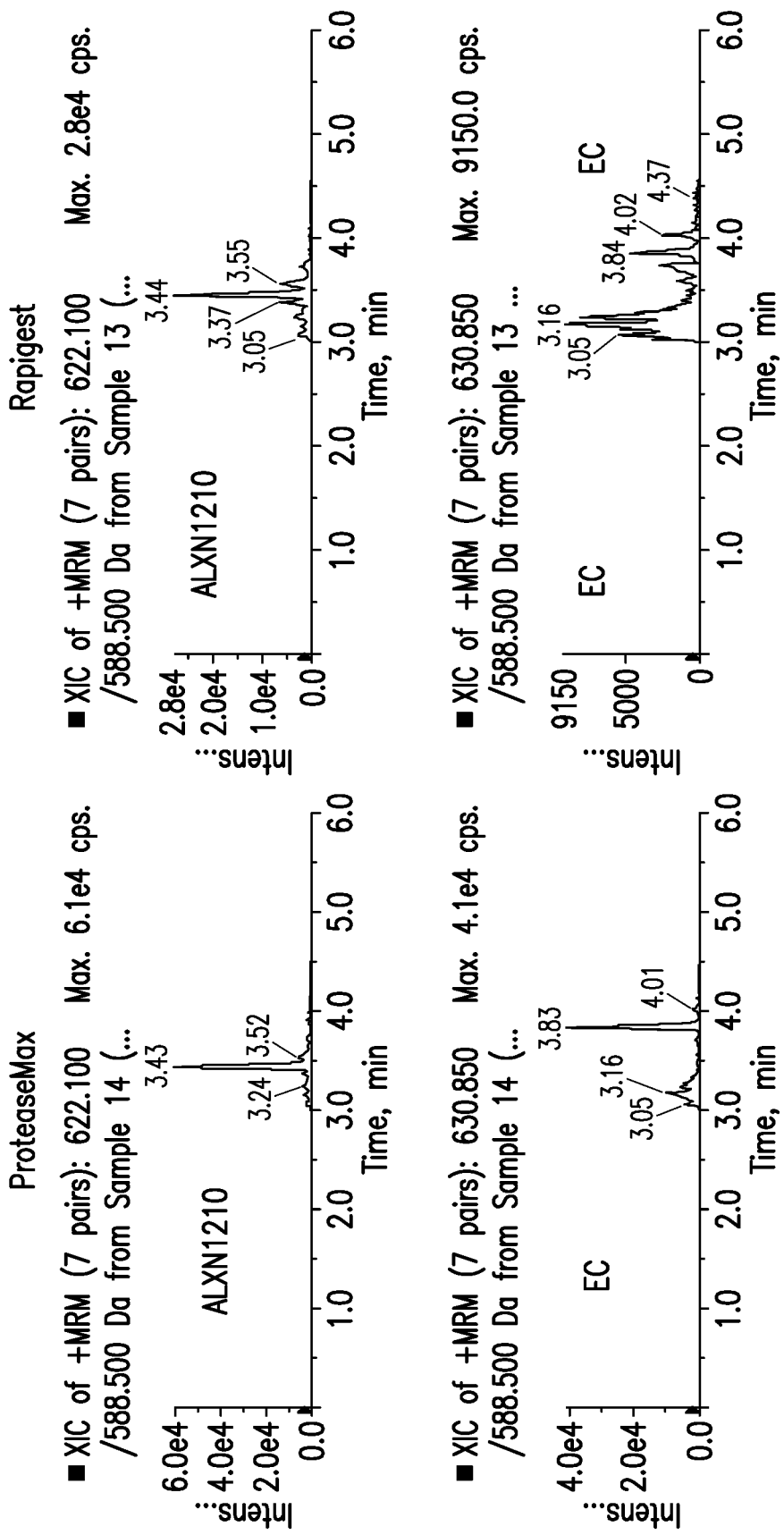
FIG. 3 shows the effect of different surfactants used during protease digestion on the ultimate signature peptide signal in mass spectrometry.
Figure 4:
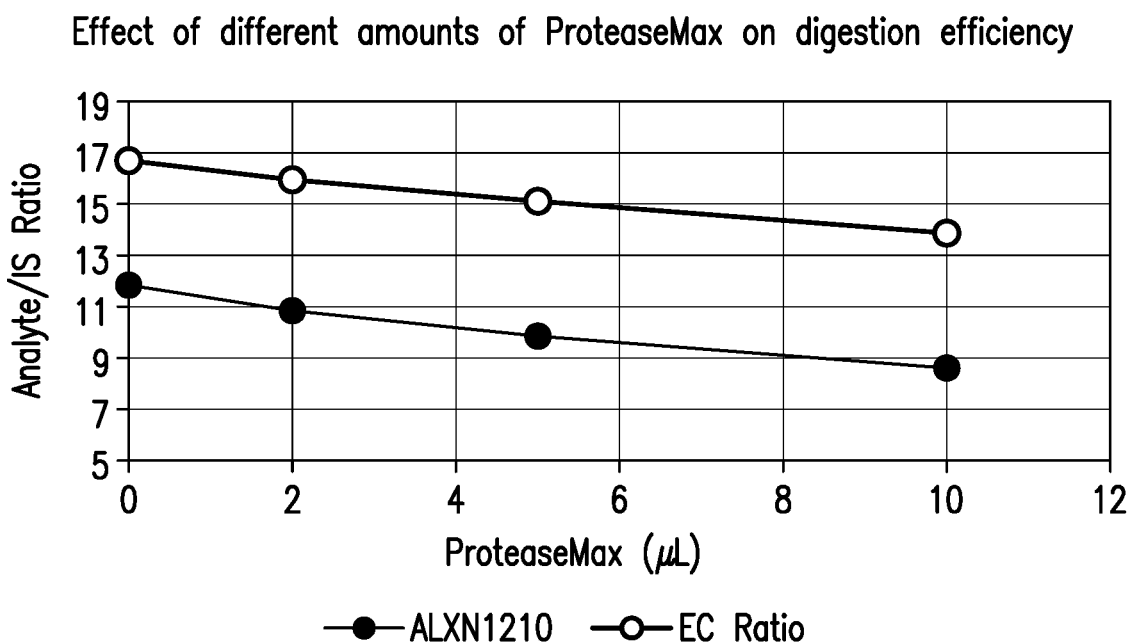
FIG. 4 shows the effect of surfactant concentration on the ratio of the analyte being measured compared to a labeled internal standard of the same peptide at a known concentration.

For trypsin digestion, certain detergents were often used to denature proteins and maintain their solubility for better digestion and recovery. During method development, RAPIGEST™, a surfactant that unfolds antibodies preferentially before proteases, was initially assessed to assist protein digestion. Alternatively, another surfactant PROTEASEMAX™ was tested for comparison, as the signature peptide recovery was less than optimal. It was found that PROTEASEMAX™ was much more effective than RAPIGEST™, as shown in FIG. 3. Surprisingly, further investigation indicated that digestion efficiency was best where there was no addition of PROTEASEMAX™, as shown in FIG. 4. Importantly, these results suggested that denaturation was not necessary for complete digestion of the antibodies and recovery and that detergents may negatively affect enzymatic digestion for certain antibodies.

Example 4: Concurrent Quantification of ALXN1210 and Eculizumab Using UPLC-MS/MS Approach Following immunocapture and protease digestion, samples of proteolytic peptide mixtures were subjected to reversed-phase UPLC-MS/MS. ALXN1210 and eculizumab were used as anti-C5 antibodies with high affinity towards complement protein C5. The assay was desirable because clinical trials were ongoing where one antibody was being switched to the other for treatment, thus quantification of their relative amounts at any given time during the switch study was necessary. The assay was further complicated due to the various levels of endogenous C5 bound to the administered antibodies, therefore the impact of the C5 concentration on signature peptide recovery from ALXN1210 and eculizumab was assessed. In addition to normal human C5 levels serum, two levels of quality control, low C5 and high C5 concentrations, were prepared to have three different levels of C5 concentrations: C5 depleted, endogenous C5 level in normal human serum, and 100 µg/mL fortified in normal human serum. As indicated below in Tables 2 and 3, C5 concentration had no impact on the detection and quantification of ALXN1210 and eculizumab, respectively.

TABLE 2

Quantification of ALXN1210 in Human Serum with Different C5 Concentrations

|  | C5 Depeleted Human Serum | | Normal Human Serum | | Normal Human Serum Fortified C5 at 100 µg/mL | |
|---|---|---|---|---|---|---|
|  | QC 31 (µg/mL) | QC 35 (µg/mL) | QC 41 (µg/mL) | QC 45 (µg/mL) | QC 51 (µg/mL) | QC 55 (µg/mL) |
|  | 2.68 | 397 | 2.7 | 337 | 2.58 | 322 |
|  | 2.34 | 403 | 2.64 | 335 | 2.43 | 326 |
|  | 2.52 | 396 | 2.73 | 344 | 2.41 | 310 |
|  | 2.87 | 370 | 2.5 | 349 | 2.51 | 354 |
|  | 2.72 | 393 | 2.61 | 365 | 2.36 | 326 |
|  | 2.62 | 387 | 2.75 | 360 | 2.23 | 336 |
| N | 6 | 6 | 6 | 6 | 6 | 6 |
| Theoretical |  |  |  |  |  |  |
| Theoretical Concentration | 2.5 | 375 | 2.5 | 375 | 2.5 | 375 |
| Mean | 2.62 | 391 | 2.66 | 348 | 2.42 | 329 |
| S.D. | 0.179 | 11.3 | 0.092 | 12.1 | 0.124 | 15 |
| % C.V. | 6.83 | 2.89 | 3.46 | 3.47 | 5.14 | 4.55 |
| % Difference from Theoretical | 4.94 | 4.27 | 6.25 | −7.15 | −3.16 | −12.3 |

TABLE 3

Quantification of Eculizumab in Human Serum with Different C5 Concentrations

|  | C5 Depeleted Human Serum | | Normal Human Serum | | Normal Human Serum Fortified C5 at 100 µg/mL | |
|---|---|---|---|---|---|---|
|  | QC 31 (µg/mL) | QC 35 (µg/mL) | QC 41 (µg/mL) | QC 45 (µg/mL) | QC 51 (µg/mL) | QC 55 (µg/mL) |
|  | 16 | 391 | 15.1 | 356 | 14.1 | 336 |
|  | 15.3 | 402 | 15.2 | 363 | 14 | 316 |
|  | 15.6 | 398 | 16 | 347 | 15.1 | 322 |
|  | 16.2 | 387 | 14.2 | 359 | 14.5 | 367 |
|  | 15.3 | 389 | 14.9 | 395 | 14.5 | 350 |
|  | 15.5 | 393 | 15.1 | 380 | 13.5 | 342 |
| N | 6 | 6 | 6 | 6 | 6 | 6 |
| Theoretical |  |  |  |  |  |  |
| Theoretical Concentration | 15 | 375 | 15 | 375 | 15 | 375 |
| Mean | 15.6 | 393 | 15.1 | 367 | 14.3 | 339 |
| S.D. | 0.35 | 5.73 | 0.566 | 17.7 | 0.525 | 18.7 |
| % C.V. | 2.23 | 1.46 | 3.75 | 4.84 | 3.67 | 5.51 |
| % Difference from Theoretical | 4.31 | 4.92 | 0.487 | −2.23 | −4.78 | −9.6 |

The effect of DMSO as a mobile phase additive was then investigated. The following chromatography conditions were used (with and without 1% DMSO):
LC Pump: One Agilent 1100 Series pump and Agilent 1200 SL series pump
Pre-column Frit: 2-µm stainless steel inline solvent filter, Upchurch Scientific-Rheodyne, Product No. A-103x
Analytical Column: Acquity BEH C8, 2.1 mm×50 mm, 1.7 µm, Waters, Product No. 1 86002877
Column Temperature: 50° C.
Pump Program: See method
Mobile Phase A: 100:0.1, Water/Formic Acid
Mobile Phase B: 100:0.1:1, Acetonitrile/Formic Acid/DMSO
Flow Rate: 0.4-0.5 mL/min
Injection Volume: 25 µL
LC Pressure: ~280 bar
Autosampler Wash 1: 5:25:30:40:0.1 TFE/IPA/Ethanol/Acetonitrile/Formic Acid, v/v/v/v/v
Autosampler Wash 2: 80:20:0.1, Water/MeOh/Formic Acid
Approximate Run Time: 7.5 min The peptide elution gradient pump program, makeup pump program, ACH valve program, MS conditions, and other parameters are shown in Tables 4, 5, 6, 7, and 8, respectively.

Figure 5:
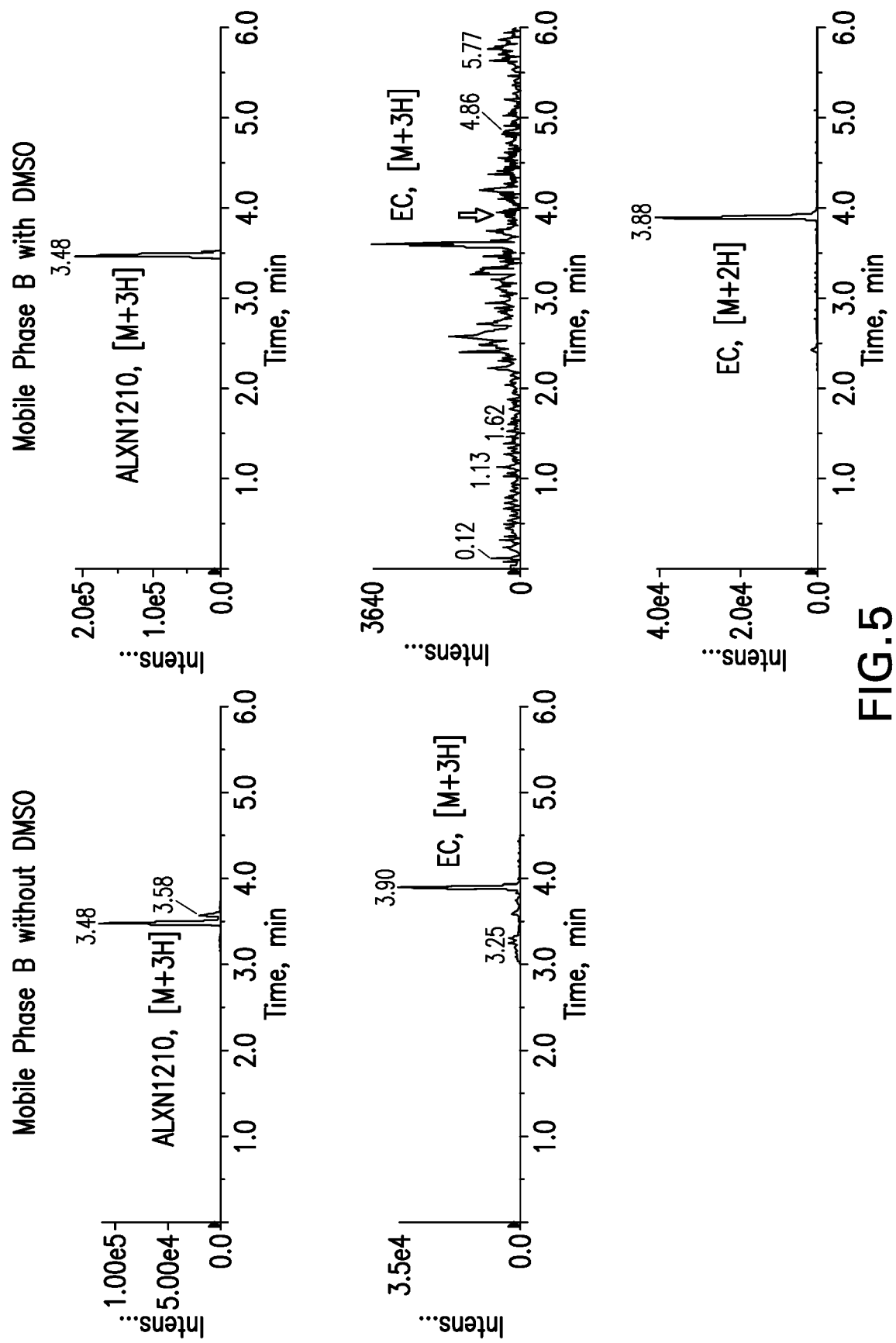
FIG. 5 shows the effect of 1% DMSO added to the mobile phase of the chromatography step of the procedure on the ultimate signal of the signature peptides in mass spectroscopy.

As shown in FIG. 5, when 1% DMSO was added to mobile phase B, the response of ALXN1210 signature peptide was doubled (DMSO, Thermo Scientific, Product No. TS20684). For eculizumab, the original precursor ion ([M+3H]) was completely converted to precursor ion [M+2H], which was selected for quantification. Sensitivity for eculizumab was increased by about 15%. The peptide elution and column washing gradient used are shown below in Table 4.

TABLE 4

Eluting Pump Program

| Step | Total Time (min) | Flow Rate (µl/min) | A (%) | B (%) |
|---|---|---|---|---|
| 0 | 0.00 | 400 | 86 | 14 |
| 1 | 1.00 | 400 | 86 | 14 |
| 2 | 4.00 | 400 | 54 | 46 |
| 3 | 4.20 | 400 | 54 | 46 |
| 4 | 4.30 | 500 | 10 | 90 |
| 5 | 5.00 | 500 | 10 | 90 |
| 6 | 5.01 | 500 | 90 | 10 |
| 7 | 5.30 | 500 | 90 | 10 |
| 8 | 5.31 | 500 | 10 | 90 |
| 9 | 6.50 | 500 | 10 | 90 |
| 10 | 6.60 | 500 | 86 | 14 |
| 11 | 7.40 | 500 | 86 | 14 |
| 12 | 7.50 | 400 | 86 | 14 |

TABLE 5

Makeup Pump Program

| Step | Total Time (min) | Flow Rate (µL/min) | A (%) | B (%) |
|---|---|---|---|---|
| 0 | 0.00 | 200 | 50 | 50 |
| 1 | 7.50 | 200 | 50 | 50 |

TABLE 6

ACH Valve Program

| Total Time (min) | Position | Comments |
|---|---|---|
| Initial | Left | Flow from Makeup pump to MS |
| 3.00 * | Right | Flow from column to MS |
| 4.00 | Left | Flow from Makeup pump to MS |
| 4.5 | Right | Flow from column to MS |
| 4.7 | Left | Flow from Makeup pump to MS |

TABLE 7

MS Conditions

| Compound ID | Q1 Mass (Da) | Q3 Mass (Da) | Dwell (msec) | DP | CE |
|---|---|---|---|---|---|
| Peptide A | 622.0 | 701.3 | 50 | 45 | 28 |
| Peptide A IS | 625.3 | 711.3 | 50 | 45 | 28 |
| Peptide B | 945.5 | 588.3 | 50 | 80 | 41 |
| Peptide B IS | 950.5 | 598.3 | 50 | 80 | 41 |

TABLE 8

Other Parameters

| Other Parameters | |
|---|---|
| CUR | 35 |
| IS | 5500 |
| TEM | 550 |
| GS1 | 60 |
| GS2 | 50 |
| CAD | 8 |
| EP | 10 |
| CXP | 5 |

Next, the carryovers from different phase columns were evaluated. A C18 reversed phase column was initially chosen for the method. Due to the relative hydrophobic nature of the two signature peptides, substantial carryovers were observed (~103% for ALXN1210 and ~118% for eculizumab peptides, comparing to LLOQ level in the blank immediately following ULOQ). A C8 column was then evaluated and the carryover for ALXN1210 and eculizumab peptides was significantly reduced to less than 50% and 30%, respectively, which was acceptable with injection order protection.

Overall, the hybrid immunocapture UPLC-MS/MS method was successfully validated for eculizumab and ALXN1210 detection and quantification using the signature tryptic peptides from each (SEQ ID NOs: 1 and 2, respectively). The standard curve range was 1.00-500 µg/mL for ALXN1210 and 5.00-500 µg/mL for eculizumab using a diluted serum sample volume of 25 µL and an MRD at 10. Linear regression was used and correlation coefficient >0.996 was observed for both mAbs during validation. Excellent intra- and inter-day assay precisions and accuracies from all quality control (QC) concentration levels were demonstrated for both ALXN1210 and eculizumab, as shown in Tables 9 and 10, respectively. The method was also successfully cross-validated with individual ligand-binding assays for ALXN1210 and eculizumab.

TABLE 9

Typical Precision and Accuracy Performance for ALXN1210

| Run ID | IA 0 (µg/mL) | IA 1 (µg/mL) | IA 2 (µg/mL) | IA 3 (µg/mL) | IA 4 (µg/mL) | IA 5 (µg/mL) |
|---|---|---|---|---|---|---|
| 1REIV2-A-1 | 0.880 | 2.34 | 4.73 | 12.6 | 74.4 | 344 |
|  | 1.00 | 2.46 | 4.77 | 15.5 | 76.7 | 375 |
|  | 0.943 | 2.04 | 5.02 | 15.0 | 77.6 | 411 |
|  | 0.961 | 2.23 | 5.08 | 15.1 | 78.6 | 396 |
|  | 0.900 | 2.68 | 4.79 | 14.9 | 78.9 | 400 |
|  | 0.926 | 2.47 | 4.45 | 14.7 | 78.7 | 395 |
| N Theoretical | 6 | 6 | 6 | 6 | 6 | 6 |
| Concentration | 1.00 | 2.50 | 5.00 | 15.0 | 75.0 | 375 |
| Mean | 0.936 | 2.37 | 4.81 | 14.6 | 77.5 | 387 |
| S.D. | 0.0439 | 0.222 | 0.228 | 1.04 | 1.71 | 24.0 |

TABLE 9-continued

Typical Precision and Accuracy Performance for ALXN1210

| Run ID | IA 0 (µg/mL) | IA 1 (µg/mL) | IA 2 (µg/mL) | IA 3 (µg/mL) | IA 4 (µg/mL) | IA 5 (µg/mL) |
|---|---|---|---|---|---|---|
| % C.V. | 4.69 | 9.36 | 4.73 | 7.10 | 2.21 | 6.19 |
| % Difference from Theoretical | −6.44 | −5.14 | −3.84 | −2.57 | 3.31 | 3.23 |

TABLE 10

Typical Precision and Accuracy Performance for Eculizumab

| Run ID | IA 2 (µg/mL) | IA 3 (µg/mL) | IA 4 (µg/mL) | IA 5 (µg/mL) |
|---|---|---|---|---|
| 1REIV2-A-2 | 5.27 | 13.3 | 75.4 | 350 |
|  | 5.98 | 15.9 | 81.3 | 386 |
|  | 5.85 | 15.3 | 80.5 | 408 |
|  | 5.69 | 15.4 | 79.5 | 395 |
|  | 5.40 | 16.0 | 83.6 | 415 |
|  | 5.20 | 16.5 | 77.3 | 395 |
| N | 6 | 6 | 6 | 6 |
| Theoretical |  |  |  |  |
| Concentration | 5.00 | 15.0 | 75.0 | 375 |
| Mean | 5.56 | 15.4 | 79.6 | 392 |
| S.D. | 0.321 | 1.13 | 2.95 | 23.1 |
| % C.V. | 5.77 | 7.35 | 3.70 | 5.89 |
| % Difference from Theoretical | 11.3 | 2.57 | 6.15 | 4.43 |

Example 5: Quantification of ALXN1210 in Human Urine

The matrix effects present in urine samples can hinder the quantification of mAbs using traditional ligand-binding assays. To overcome these challenges, the UPLC-MS/MS method described above was optimized to quantify ALXN1210 in human urine. Briefly, ALXN1210 was subject to denaturation, reduction with dithiothreitol (DTT) at 65° C., alkylation with iodoacetamide, and trypsin digestion. The signature peptide generated from ALXN1210 (SEQ ID NO: 2), was then used for the quantification of ALXN1210 using UPLC-MS/MS. Tables 11 and 12 list the equipment and reagents used, respectively.

TABLE 11

Equipment

| Equipment | Vendor/Model |
|---|---|
| SPE System | Agela, SPE-M96 Positive Pressure SPE Device |
| 1.4 mL Non-coded Push Cap Tubes U-bottom* | Micronic, MP 32022 |
| 96-Well Square Well Plate, 2.0 mL per well | Micro Liter, Product# 07-7400 |
| Mass Spectrometer | SCIEX6500 |
| Micro-Analytical Balance | Capable of weighing 0.001 mg |
| Analytical Balance | Capable of weighing 0.01 mg |
| Water System | Sys#. 56-2 |
| Vortex Mixer | VWR, VX-2500 |
| Advantage Plug Cap Strips | Analytical sales and service: Cat#96128-2 |
| Disposable sterile pipet tips with extended length and ultrafine point | VWR, VWR#37001-524 |
| Eppendorf MixMate | Eppendorf, Product No. 5353 |
| 96 well silicone mat | Agela, Cat#96GP2036-M |
| Protein LoBind tube, 2 mL | Eppendorf, Product No. 022431102 |
| Cleanert PEP 96-well SPE Microplate, 5 mg/1 mL/well | Agela, Cat#PE00501-MW |
| Analytical Column | Acquity BEH C8, 2.1 mm × 50 mm, 1.7 m, Waters, Product No. 186002877 |

TABLE 12

Reagents

| Item Description | Vendor |
|---|---|
| HPLC Grade Acetonitrile (ACN) | Fisher |
| Water | Purified |
| GR Grade Formic Acid (FA) | ACROS |
| GR Grade Ammonium Bicarbonate | VWR |
| HPLC Grade Methanol (MeOH) | Fisher |
| HPLC Grade Isopropanol (IPA) | Fisher |
| DL-Dithiothreitol (DTT) | Sigma, Product No. D0632-10G |
| Iodoacetamide (IAA) | Sigma, Product No. I1149-5G |
| MS Grade Trypsin Protease | Pierce, Product No. 90059 |
| RAPIGEST ™ Box of (5) 1 mg vials | Waters Product# 186001861 |
| Human Urine | BioreclamationIVT |
| HPLC Grade Dimethylsulfoxide (DMSO) | Thermo Scientific |

Carryover was one of the major technical challenges during development of the assay for detection of ALXN1210 and eculizumab in human serum. The HPLC gradient of the assay for human urine was improved to include a higher starting mobile phase B percentage (from 14% to 25%). This change resulted in no detectable carryover and the elimination of an additional column wash cycle, which led to shorter sample run time. The carryover performance during validation is shown in Table 13.

TABLE 13

Injection Carryover Results for ALXN1210

| Run Date | Watson Run ID | Sequence No. | Double Blank Sample Analyte Peak Area | IS Peak Area | STD 1 Sample Analyte Peak Area | Mean IS Peak Area from Accepted Stds and QC | Carryover % Analyte | IS |
|---|---|---|---|---|---|---|---|---|
|  |  | 14 | 0 | 0 |  |  | 0.0 | 0.0 |
| 16 Jun 2017 | 1 | 15 | 0 | 0 | 4294 | 509613 | 0.0 | 0.0 |
|  |  | 16 | 0 | 0 |  |  | 0.0 | 0.0 |
|  |  | 14 | 0 | 0 |  |  | 0.0 | 0.0 |
| 16 Jun 2017 | 2 | 15 | 0 | 0 | 5289 | 633759 | 0.0 | 0.0 |
|  |  | 16 | 0 | 0 |  |  | 0.0 | 0.0 |
|  |  | 14 | 0 | 0 |  |  | 0.0 | 0.0 |
| 19 Jun 2017 | 3 | 15 | 0 | 0 | 5585 | 586840 | 0.0 | 0.0 |
|  |  | 16 | 0 | 0 |  |  | 0.0 | 0.0 |
|  |  | 14 | 0 | 0 |  |  | 0.0 | 0.0 |
| 20 Jun 2017 | 4 | 15 | 0 | 0 | 5592 | 680500 | 0.0 | 0.0 |
|  |  | 16 | 0 | 0 |  |  | 0.0 | 0.0 |

Additional testing was conducted to evaluate the performance of the assay under conditions of elevated protein and red blood cell (hemolyzed) levels, as they are often present in patients' urine. Urine Interference Quality Control (QC) samples were prepared containing 15% serum or 2% hemolyzed whole blood (volume %). Standard samples ("std-") did not contain any serum or hemolyzed blood. The recovery of ALXN1210 signature peptide at low QC level with 15% serum was substantially reduced in comparison to the calibration curve and QC samples prepared in a 100% urine matrix, as shown in Table 14.

TABLE 14

Recovery of the QC samples with serum and hemolyzed whole blood

| Sample Name | Accuracy (%) | Analyte Concentration (μg/mL) | Calculated Concentration (μg/mL) | Analyte Peak Area (counts) | IS Peak Area (counts) |
|---|---|---|---|---|---|
| Std-1 | 103.46 | 0.08 | 0.083 | 612 | 182644 |
| Std-2 | 94.86 | 0.16 | 0.152 | 1396 | 198555 |
| Std-3 | 89.79 | 1 | 0.898 | 10427 | 222809 |
| Std-4 | 91.73 | 5 | 4.587 | 57254 | 235224 |
| Std-5 | 99.53 | 10 | 9.953 | 129894 | 245341 |
| Std-6 | 106.95 | 20 | 21.391 | 306661 | 269217 |
| Std-7 | 107.31 | 32 | 34.341 | 522564 | 285664 |
| Std-8 | 106.35 | 40 | 42.541 | 678037 | 299169 |

TABLE 14-continued

Recovery of the QC samples with serum and hemolyzed whole blood

| Sample Name | Accuracy (%) | Analyte Concentration (μg/mL) | Calculated Concentration (μg/mL) | Analyte Peak Area (counts) | IS Peak Area (counts) |
|---|---|---|---|---|---|
| 15% Srum-Q2-1 | 17.08 | 5 | 0.854 | 3137 | 70549 |
| 15% Srum-Q2-2 | 15.39 | 5 | 0.77 | 2453 | 61381 |
| 15% Srum-Q2-3 | 17.86 | 5 | 0.893 | 865 | 18582 |
| 15% Srum-Q2-4 | 13.55 | 5 | 0.678 | 636 | 18155 |
| 15% Srum-Q2-5 | 20.82 | 5 | 1.041 | 807 | 14836 |
| 15% Srum-Q2-6 | 14.12 | 5 | 0.706 | 504 | 13794 |

Figure 7:
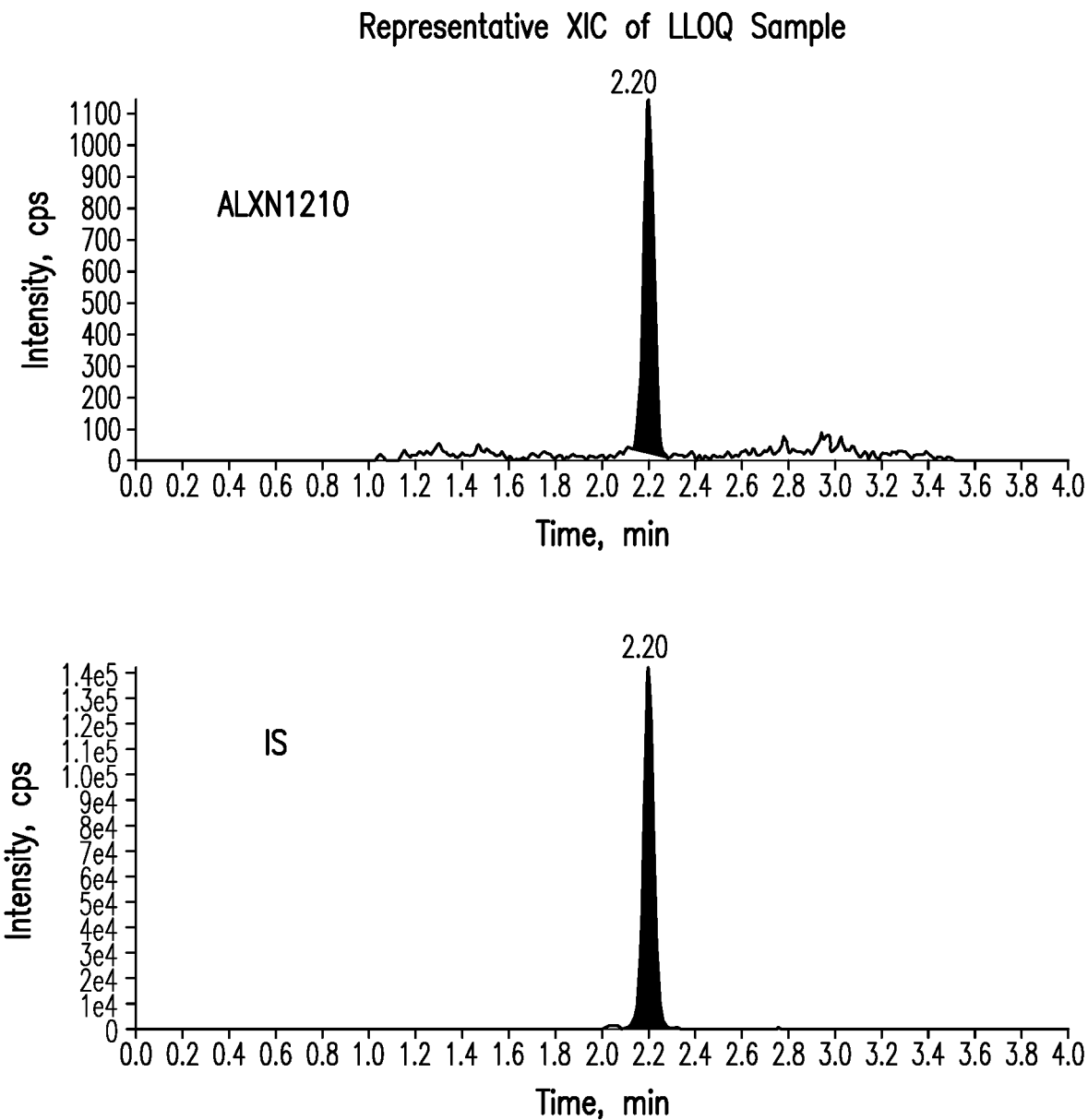
FIG. 7 shows a representative extracted ion chromatogram (XIC) of an LLOQ sample.

Human serum was added to all of the samples (5% volume of the sample) during sample processing to normalize calibration curve QCs and the QC samples containing serum or hemolyzed whole blood. Standard samples ("std-") and plate acceptance QC samples ("Low-", "Mid-", and "High-") did not contain any serum or hemolyzed blood. Digestion duration was then prolonged to enhance the recovery of ALXN1210 signature peptide in urine samples containing human serum. The conditions had good recovery at both 15% serum and 2% hemolyzed whole blood at LLOQ QC level, as shown in Table 15. The assay also had good sensitivity with a 20 μl sample volume. Representative extracted ion chromatograms (XIC) of blank and LLOQ are shown in FIGS. 6 and 7.

TABLE 15

Recovery of the QC samples containing serum or hemolyzed whole blood with the addition of human serum and overnight tryptic digestion

| Sample Name | Accuracy (%) | Analyte Concentration (ng/mL) | Calculated Concentration (ng/mL) | Area Ratio | Analyte Peak Area (counts) | IS Peak Area (counts) |
|---|---|---|---|---|---|---|
| Std1 | 97.36 | 0.08 | 0.078 | 0.00734 | 236 | 32120 |
| Std2 | 91.71 | 0.16 | 0.147 | 0.01432 | 407 | 28409 |
| Std3 | 101.44 | 1 | 1.014 | 0.1023 | 3358 | 32826 |
| Std4 | 103.27 | 5 | 5.164 | 0.52304 | 15635 | 29892 |
| Std5 | 95.66 | 10 | 9.566 | 0.9695 | 30695 | 31660 |
| Std6 | 106.72 | 20 | 21.345 | 2.16388 | 67566 | 31224 |
| Std7 | 107 | 32 | 34.241 | 3.4716 | 107142 | 30862 |
| Std8 | 102.23 | 40 | 40.891 | 4.14592 | 130912 | 31576 |
| 15% Serum-LLOQ-1 | 119.11 | 0.08 | 0.095 | 0.0091 | 269 | 29549 |
| 15% Serum-LLOQ-2 | 104.53 | 0.08 | 0.084 | 0.00792 | 261 | 32897 |
| 15% Serum-LLOQ-3 | 101.92 | 0.08 | 0.082 | 0.00771 | 228 | 29620 |

TABLE 15-continued

Recovery of the QC samples containing serum or hemolyzed whole blood with the addition of human serum and overnight tryptic digestion

| Sample Name | Accuracy (%) | Analyte Concentration (ng/mL) | Calculated Concentration (ng/mL) | Area Ratio | Analyte Peak Area (counts) | IS Peak Area (counts) |
|---|---|---|---|---|---|---|
| 15% Serum-LLOQ-4 | 112.57 | 0.08 | 0.09 | 0.00857 | 256 | 29818 |
| 15% Serum-LLOQ-5 | 98.29 | 0.08 | 0.079 | 0.00741 | 204 | 27577 |
| 15% Serum-LLOQ-6 | 93.5 | 0.08 | 0.075 | 0.00702 | 213 | 30352 |
| 2% Hem-LLOQ-1 | 105.4 | 0.08 | 0.084 | 0.00799 | 293 | 36720 |
| 2% Hem-LLOQ-2 | 103.03 | 0.08 | 0.082 | 0.0078 | 298 | 38204 |
| 2% Hem-LLOQ-3 | 84.7 | 0.08 | 0.068 | 0.00631 | 245 | 38790 |
| 2% Hem-LLOQ-4 | 93.49 | 0.08 | 0.075 | 0.00702 | 172 | 24496 |
| 2% Hem-LLOQ-5 | 81.42 | 0.08 | 0.065 | 0.00604 | 160 | 26390 |
| 2% Hem-LLOQ-6 | 96.11 | 0.08 | 0.077 | 0.00724 | 209 | 28868 |
| Low-1 | 86.67 | 0.24 | 0.208 | 0.02053 | 600 | 29217 |
| Mid-1 | 93.94 | 5 | 4.697 | 0.47574 | 12131 | 25500 |
| High-1 | 110.27 | 30 | 33.082 | 3.35413 | 99122 | 29552 |
| Low-2 | 89 | 0.24 | 0.214 | 0.0211 | 704 | 33350 |
| Mid-2 | 98.26 | 5 | 4.913 | 0.49766 | 17907 | 35982 |
| High-2 | 107.49 | 30 | 32.248 | 3.26953 | 95121 | 29093 |

In summary, the UPLC-MS/MS method was successfully developed and validated for the quantitation of ALXN1210 in human urine using a signature tryptic peptide. With a sample volume of 20 μL, the calibration curve range of the assay was 0.0800-40.0 μm/mL for ALXN1210. Samples above the ULOQ could be diluted up to 10 fold and 2 fold using pooled human urine (data not shown). Excellent intra- and inter-day assay precisions and accuracies from all quality control (QC) concentration levels were demonstrated in addition to linearity, recovery, dilution integrity, processed sample stability, QC bench-top stability, matrix effect, batch-size, reinjection stability, QC freeze/thaw stability, carry-over, and interference from analyte on IS (data not shown). This method demonstrates the capability of the UPLC-MS/MS method to overcome the matrix effect in urine and quantify ALXN1210 with excellent sensitivity.

SEQUENCE LISTING amino acid sequence for eculizumab signature peptide
SEQ ID NO: 1
ASGYIFSNYWIQWVR amino acid sequence for ALXN1210 signature peptide
SEQ ID NO: 2
ASGHIFSNYWIQWVR amino acid sequence of heavy chain CDR1 of eculizumab (as defined under combined Kabat-Chothia definition)
SEQ ID NO: 3
GYIFSNYWIQ amino acid sequence of heavy chain CDR2 of eculizumab (as defined under Kabat definition)
SEQ ID NO: 4
EILPGSGSTEYTENFKD amino acid sequence of the heavy chain CDR3 of eculizumab and ALXN1210 (as defined under combined Kabat definition).
SEQ ID NO: 5
YFFGSSPNWYFDV

SEQUENCE LISTING -continued amino acid sequence of the light chain CDR1 of eculizumab and ALXN1210 (as defined under Kabat definition)
SEQ ID NO: 6
GASENIYGALN amino acid sequence of light chain CDR2 of eculizumab and ALXN1210 (as defined under Kabat definition)
SEQ ID NO: 7
GATNLAD amino acid sequence of light chain CDR3 of eculizumab and ALXN1210 (as defined under Kabat definition)
SEQ ID NO: 8
QNVLNTPLT amino acid sequence of heavy chain variable region of eculizumab
SEQ ID NO: 9
QVQLVQSGAEVKKPGASVKVSCKASGYIFSNYWIQWVRQAPGQGLEW
MGEILPGSGSTEYTENFKDRVTMTRDTSTSTVYMELSSLRSEDTAVY
YCARYFFGSSPNWYFDVWGQGTLVTVSS amino acid sequence of light chain variable region of eculizumab and ALXN1210
SEQ ID NO: 10
DIQMTQSPSSLSASVGDRVTITCGASENIYGALNWYQQKPGKAPKLL
IYGATNLADGVPSRFSGSGSGTDFTLTISSLQPEDFATYYCQNVLNT
PLTFGQGTKVEIK amino acid sequence of heavy chain constant region of eculizumab
SEQ ID NO: 11
ASTKGPSVFPLAPCSRSTSESTAALGCLVKDYFPEPVTVSWNSGALT
SGVHTFPAVLQSSGLYSLSSVVTVPSSNFGTQTYTCNVDHKPSNTKV
DKTVERKCCVECPPCPAPPVAGPSVFLFPPKPKDTLMISRTPEVTCV
VVDVSQEDPEVQFNWYVDGVEVHNAKTKPREEQFNSTYRVVSVLTVL
HQDWLNGKEYKCKVSNKGLPSSIEKTISKAKGQPREPQVYTLPPSQE

SEQUENCE LISTING

EMTKNQVSLTCLVKGFYPSDIAVEWESNGQPENNYKTTPPVLDSDGS

FFLYSRLTVDKSRWQEGNVFSCSVMHEALHNHYTQKSLSLSLGK amino acid sequence of entire heavy chain of eculizumab
SEQ ID NO: 12

QVQLVQSGAEVKKPGASVKVSCKASGYIFSNYWIQWVRQAPGQGLEW

MGEILPGSGSTEYTENFKDRVTMTRDTSTSTVYMELSSLRSEDTAVY

YCARYFFGSSPNWYFDVWGQGTLVTVSSASTKGPSVFPLAPCSRSTS

ESTAALGCLVKDYFPEPVTVSWNSGALTSGVHTFPAVLQSSGLYSLS

SVVTVPSSNFGTQTYTCNVDHKPSNTKVDKTVERKCCVECPPCPAPP

VAGPSVFLFPPKPKDTLMISRTPEVTCVVVDVSQEDPEVQFNWYVDG

VEVHNAKTKPREEQFNSTYRVVSVLTVLHQDWLNGKEYKCKVSNKGL

PSSIEKTISKAKGQPREPQVYTLPPSQEEMTKNQVSLTCLVKGFYPS

DIAVEWESNGQPENNYKTTPPVLDSDGSFFLYSRLTVDKSRWQEGNV

FSCSVMHEALHNHYTQKSLSLSLGK amino acid sequence of entire light chain of eculizumab and ALXN1210
SEQ ID NO: 13

DIQMTQSPSSLSASVGDRVTITCGASENIYGALNWYQQKPGKAPKLL

IYGATNLADGVPSRFSGSGSGTDFTLTISSLQPEDFATYYCQNVLNT

PLTFGQGTKVEIKRTVAAPSVFIFPPSDEQLKSGTASVVCLLNNFYP

REAKVQWKVDNALQSGNSQESVTEQDSKDSTYSLSSTLTLSKADYEK

HKVYACEVTHQGLSSPVTKSFNRGEC amino acid sequence of heavy chain variable region of ALXN1210
SEQ ID NO: 14

QVQLVQSGAEVKKPGASVKVSCKASGHIFSNYWIQWVRQAPGQGLEW

MGEILPGSGHTEYTENFKDRVTMTRDTSTSTVYMELSSLRSEDTAVY

YCARYFFGSSPNWYFDVWGQGTLVTVSS amino acid sequence of heavy chain constant region of ALXN1210
SEQ ID NO: 15

ASTKGPSVFPLAPCSRSTSESTAALGCLVKDYFPEPVTVSWNSGALT

SGVHTFPAVLQSSGLYSLSSVVTVPSSNFGTQTYTCNVDHKPSNTKV

DKTVERKCCVECPPCPAPPVAGPSVFLFPPKPKDTLMISRTPEVTCV

VVDVSQEDPEVQFNWYVDGVEVHNAKTKPREEQFNSTYRVVSVLTVL

HQDWLNGKEYKCKVSNKGLPSSIEKTISKAKGQPREPQVYTLPPSQE

EMTKNQVSLTCLVKGFYPSDIAVEWESNGQPENNYKTTPPVLDSDGS

FFLYSRLTVDKSRWQEGNVFSCSVLHEALHSHYTQKSLSLSLGK amino acid sequence of entire heavy chain of ALXN1210
SEQ ID NO: 16

QVQLVQSGAEVKKPGASVKVSCKASGHIFSNYWIQWVRQAPGQGLEW

MGEILPGSGHTEYTENFKDRVTMTRDTSTSTVYMELSSLRSEDTAVY

YCARYFFGSSPNWYFDVWGQGTLVTVSSASTKGPSVFPLAPCSRSTS

ESTAALGCLVKDYFPEPVTVSWNSGALTSGVHTFPAVLQSSGLYSLS

SVVTVPSSNFGTQTYTCNVDHKPSNTKVDKTVERKCCVECPPCPAPP

VAGPSVFLFPPKPKDTLMISRTPEVTCVVVDVSQEDPEVQFNWYVDG

VEVHNAKTKPREEQFNSTYRVVSVLTVLHQDWLNGKEYKCKVSNKGL

PSSIEKTISKAKGQPREPQVYTLPPSQEEMTKNQVSLTCLVKGFYPS

DIAVEWESNGQPENNYKTTPPVLDSDGSFFLYSRLTVDKSRWQEGNV

FSCSVLHEALHSHYTQKSLSLSLGK amino acid sequence of heavy chain CDR1 of ALXN1210
SEQ ID NO: 17

GHIFSNYWIQ amino acid sequence of heavy chain CDR2 of ALXN1210
SEQ ID NO: 18

EILPGSGHTEYTENFKD amino acid sequence for eculizumab candidate signature peptide
SEQ ID NO: 19

QAPGQGLEWMGEILPGSGSTEYTENFK amino acid sequence for eculizumab candidate signature peptide
SEQ ID NO: 20

WQEGNVFSCSVMHEALHNHYTQK amino acid sequence for ALXN1210 candidate signature peptide
SEQ ID NO: 21

QAPGQGLEWMGEILPGSGHTEYTENFK amino acid sequence for ALXN1210 candidate signature peptide
SEQ ID NO: 22

WQEGNVFSCSVLHEALHSHYTQK

We claim:

1. A method of detecting and quantifying the respective amounts of two antibodies having high sequence identity present together in a biological sample, wherein the antibodies are eculizumab and ravulizumab, the method comprising:
   (a) treating the biological sample containing the antibodies with a protease to form a proteolytic peptide mixture of the antibodies in the biological sample;
   (b) analyzing a sample of the proteolytic peptide mixture by high performance liquid chromatography (HPLC) tandem mass spectrometry to detect a signature peptide from each of the antibodies in the biological sample, wherein the signature peptide for eculizumab comprises SEQ ID NO: 1, SEQ ID NO: 19, or SEQ ID NO: 20, and the signature peptide for ravulizumab comprises SEQ ID NO: 2, SEQ ID NO: 21, or SEQ ID NO:22 wherein the signature peptide comprises no more than 27 amino acids; and
   (c) quantifying each antibody in the biological sample based on the signal ratio of its signature peptide to an internal control, wherein the internal control comprises a labeled form of the same signature peptide.

2. A method of detecting and quantifying the amount of an antibody present in a biological sample, wherein the antibody is eculizumab, the method comprising:
   (a) treating the biological sample containing the antibody with a protease to form a proteolytic peptide mixture of the antibody in the biological sample;
   (b) analyzing a sample of the proteolytic peptide mixture by high performance liquid chromatography (HPLC) tandem mass spectrometry to detect a signature peptide, wherein the signature peptide comprises SEQ ID NO: 1, SEQ ID NO: 19, or SEQ ID NO: 20 and wherein the signature peptide comprises no more than 27 amino acids; and
   (c) quantifying the amount of eculizumab in the biological sample based on the signal ratio of the signature peptide to an internal control, wherein the internal control comprises a labeled form of the same signature peptide.

3. A method of detecting and quantifying the amount of an antibody present in a biological sample, wherein the antibody is ravulizumab, the method comprising:
   (a) treating the biological sample containing the antibody with a protease to form a proteolytic peptide mixture of the antibody in the biological sample;
   (b) analyzing a sample of the proteolytic peptide mixture by high performance liquid chromatography (HPLC) tandem mass spectrometry to detect a signature peptide, wherein the signature peptide comprises SEQ ID NO: 2, SEQ ID NO: 21, or SEQ ID NO:22 wherein the signature peptide comprises no more than 27 amino acids; and
   (c) quantifying the amount of ravulizumab in the biological sample based on the signal ratio of the signature peptide to an internal control, wherein the internal control comprises a labeled form of the same signature peptide.

4. The method of claim 2, wherein the protease is trypsin.

5. The method of claim 2, further comprising:
   (a) contacting the biological sample with an affinity capture reagent prior to treating the biological sample with a protease;
   (b) washing the Protein A bound antibodies to remove unbound components prior to proteolysis;
   (c) denaturing the antibody sample;
   (d) reducing the antibody sample; and/or
   (e) alkylating the antibody sample.

6. The method of claim 5, wherein the affinity capture reagent is bead-supported Protein A.

7. The method of claim 5, wherein the denaturation, reduction, and alkylation steps unfold the antibody protein and facilitates proteolytic digestion.

8. The method of claim 2, wherein the mass spectrometry is reverse-phase UPLC-MS/MS.

9. The method of claim 2, wherein the biological sample is serum or urine.

10. The method of claim 2, wherein the signature peptide comprises no more than 15 amino acids.

11. An isolated peptide consisting of SEQ ID NO: 1, SEQ ID NO: 2, SEQ ID NO: 19, SEQ ID NO: 21, or SEQ ID NO: 22.

12. The method of claim 1, wherein the wherein the signature peptide for eculizumab comprises SEQ ID NO: 1.

13. The method of claim 1, wherein the wherein the signature peptide for eculizumab comprises SEQ ID NO: 19.

14. The method of claim 1, wherein the wherein the signature peptide for eculizumab comprises SEQ ID NO: 20.

15. The method of claim 1, wherein the wherein the signature peptide for ravulizumab comprises SEQ ID NO: 2.

16. The method of claim 1, wherein the wherein the signature peptide for ravulizumab comprises SEQ ID NO: 21.

17. The method of claim 1, wherein the wherein the signature peptide for ravulizumab comprises SEQ ID NO: 22.

18. The method of claim 2, wherein the wherein the signature peptide comprises SEQ ID NO: 1.

19. The method of claim 2, wherein the wherein the signature peptide comprises SEQ ID NO: 19.

20. The method of claim 2, wherein the wherein the signature peptide comprises SEQ ID NO: 20.

21. The method of claim 3, wherein the wherein the signature peptide comprises SEQ ID NO: 2.

22. The method of claim 3, wherein the wherein the signature peptide comprises SEQ ID NO: 21.

23. The method of claim 3, wherein the wherein the signature peptide comprises SEQ ID NO: 22.

24. The isolated peptide of claim 11, wherein the peptide consists of SEQ ID NO: 1.

25. The isolated peptide of claim 11, wherein the peptide consists of SEQ ID NO: 2.

26. The isolated peptide of claim 11, wherein the peptide consists of SEQ ID NO: 19.

27. The isolated peptide of claim 11, wherein the peptide consists of SEQ ID NO: 21.

28. The isolated peptide of claim 11, wherein the peptide consists of SEQ ID NO: 22.

* * * * *